US012565513B2

(12) United States Patent

Guo et al.

(10) Patent No.: US 12,565,513 B2

(45) Date of Patent: Mar. 3, 2026

(54) SYNTHESIS OF GLYCOSPHINGOLIPIDS

(71) Applicant: University of Florida Research Foundation, Inc., Gainesville, FL (US)

(72) Inventors: Zhongwu Guo, Gainesville, FL (US); Qingjiang Li, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 991 days.

(21) Appl. No.: 17/761,109

(22) PCT Filed: Sep. 17, 2020

(86) PCT No.: PCT/US2020/051172

§ 371 (c)(1),
(2) Date: Mar. 16, 2022

(87) PCT Pub. No.: WO2021/055539

PCT Pub. Date: Mar. 25, 2021

(65) Prior Publication Data

US 2022/0340612 A1 Oct. 27, 2022

Related U.S. Application Data

(60) Provisional application No. 62/901,609, filed on Sep. 17, 2019.

(51) Int. Cl.
*C07H 15/10* (2006.01)

(52) U.S. Cl.
CPC .................................... *C07H 15/10* (2013.01)

(58) Field of Classification Search
None
See application file for complete search history.

(56) References Cited

U.S. PATENT DOCUMENTS

2005/0032742 A1 2/2005 Defrees et al.

FOREIGN PATENT DOCUMENTS

WO 2003/101937 A1 12/2003

OTHER PUBLICATIONS

Zheng et al., Tetrahedron, vol. 68, pp. 1475-1482, 2012. (Year: 2012).*

Sandbhor et al., Biochemistry, vol. 50, pp. 6753-6762, 2011 . (Year: 2011).*

Santra et al., Chemical Communications (Cambridge, UK), 2017, 53(59), pp. 8280-8283. (Year: 2017).*

Adlercreutz et al., Thiogalactopyranosides are Resistant to Hydrolysis by alpha-Galactosidases, ChemBioChem, 13:1673-1679 (2012).

Ando et al., First total synthesis of a-(2?3)/a-(2?6)-disialyl lactotetraosyl ceramide and disialyl Lewis A ganglioside as cancer-associated carbohydrate antigens, Carbohydr. Res., 338:503-514 (2003).

Ariga et al., The pathological roles of ganglioside metabolism in Alzheimer's disease: Effects of gangliosides on neurogenesis, Int. J. Alzh. Dis., 2011:ID 193618 (2011).

Baer et al., Glycosylimidate, 35 Synthese eines Cerebrosids mit (4E,8E)-Sphingadienin-Struktur aus Tetragonia tetragonoides mit antiulcerogener Aktivität, Liebigs Ann. der Chem., 1988:669-674 (1988).

Boland et al., Phosphorylated glycosphingolipids essential for cholesterol mobilization in Caenorhabditis elegans, Nat. Chem. Biol., 13:647-654 (2017).

Calderin et al., A New and Efficient Approach to Prepare N-Acetyl GM3 Ganglioside via Trisaccharide [ 1-4 ] Lactone, Org. Process Res. Dev., 17:53-60 (2013).

Castro-Palomino et al., Synthesis of ganglioside GD3 and its comparison with bovine GD3 with regard to oligodendrocyte apoptosis mitochondrial damage, Chem. Eur. J., 7:2178-2184 (2001).

Chaudhary et al., Synthesis of Fungal Glycolipid Asperamide B and Investigation of Its Ability to Stimulate Natural Killer T Cells, Org. Lett., 15:5242-5245 (2013).

Chen et al., Synthesis and Structure-Activity Relationship Study of Isoglobotrihexosylceramide Analogues, J. Org. Chem., 72:9914-9923 (2007).

Cheng et al., A divergent approach to the synthesis of iGb3 sugar and lipid analogues via a lactosyl 2-azido-sphingosine intermediate, Org. Biomol. Chem., 12:2729-2736 (2014).

D'Angelo et al., Glycosphingolipids: synthesis and functions. FEBS J., 280:6336-6353 (2013).

Daikoku et al., Fluorescence-monitored zero dead-volume nanoLC-microESI-QIT-TOF MS for analysis of fluorescently tagged glycosphingolipids, Analyst, 136:1046-1050 (2011).

Degroote et al., The cell biology of glycosphingolipids, Semin. Cell Dev. Biol., 15:375-387 (2004).

Duclos, The total synthesis of ganglioside GM3, Carbohydr. Res., 328:489-507 (2000).

Echten-Deckert et al., Sphingolipids: Critical players in Alzheimer's disease, Prog. Lipid Res., 51:378-393 (2012).

Figueroa-Perez et al., Total synthesis of alpha-galactosyl cerebroside, Carbohydr. Res., 328:95-102 (2000).

Gao et al., Total Synthesis of Marine Glycosphingolipid Vesparioside B, J. Am. Chem. Soc., 138:1684-1688 (2016).

Garcia-Ruiz et al., Glycosphingolipids and cell death: one aim, many ways, Apoptosis, 20:607-620 (2015).

Gaudino et al., A Novel and Efficient Synthesis of Neolacto Series Gangliosides 3'-nLM1 and 6'-nLM1, J. Am. Chem. Soc., 116:1149-1150 (1994).

(Continued)

*Primary Examiner* — Traviss C McIntosh, III

(74) *Attorney, Agent, or Firm* — MARSHALL, GERSTEIN & BORUN LLP

(57) ABSTRACT

Provided are methods of synthesizing glycolipids. The methods combine chemical and enzymatic transformations to rapidly provide diverse natural and functionalized glycolipids in a high convergent matter. Stepwise enzymatic elongation of a carbohydrate chain of a common glycolipid precursor, compound (1), provides glycan intermediates of Formula (II), using sugar-nucleotides as glycosyl donors and glycosyltransferases as enzymes. Also provided are glycan intermediates of Formula (II) and alkene intermediates of Formula (IV) and methods of preparing same.

20 Claims, No Drawings

(56) References Cited

OTHER PUBLICATIONS

Gege et al., Synthesis of fluorescence labeled sialyl Lewisx glycosphingolipids, Tetrahedron Lett., 42:377-380 (2001).
Gege et al., Total synthesis of the natural antigen involved in the hyperacute rejection response to xenotransplants, Carbohydr. Res., 328:459-466 (2000).
Gege et al., Visualization of sialyl LewisX glycosphingolipid microdomains in model membranes as selectin recognition motifs using a fluorescence label, Carbohydr. Res., 343:2361-2368 (2008).
Ginzburg et al., The pathogenesis of glycosphingolipid storage disorders, Semin. Cell Dev. Biol., 15:417-431 (2004).
Gold et al., A Concise Synthesis of Globotriaosylsphingosine, Eur. J. Org. Chem., 2011:1652-1663 (2011).
Goto et al., Total Synthesis and Neuritogenic Activity Evaluation of Ganglioside PNG-2A from the Starfish Protoreaster nodosus, Asian J. Org. Chem., 4:1160-1171 (2015).
Gouaze-Andersson et al., Glycosphingolipids and drug resistance, Biochim. Biophys. Acta., 1758:2096-2103 (2006).
Groux-Degroote et al., Gangliosides: Structures, Biosynthesis, Analysis, and Roles in Cancer, ChemBioChem., 18:1146-1154 (2017).
Hada et al., Stereoselective synthesis of 1,2-cis galactosides: synthesis of a glycolipid containing Gala1-6Gal component from *Zygomycetes* species, Tetrahedron Lett., 47:6647-6650 (2006).
Hada et al., Synthesis of neutral glycosphingolipids from Zygomycetes, Carbohydr. Res., 343:2315-2324 (2008).
Hada et al., Synthetic studies on glycosphingolipids from Protostomia phyla: syntheses and biological activities of amphoteric glycolipids containing a phosphocholine residue from the earthworm Pheretima hilgendorfi, Carbohydr. Res., 343:2221-2228 (2008).
Hada et al., Synthetic studies on novel fucosylated glycosphingolipids from the millipede, Parafontaria laminata armigera, Tetrahedron Lett., 41:9065-9068 (2000).
Halmer et al., Sphingolipids: Important Players in Multiple Sclerosis, Cell Physiol. Biochem., 34:111-118 (2014).
Hancock et al., Designer enzymes for glycosphingolipid synthesis by directed evolution, Nat. Chem. Biol., 5:508-514 (2009).
Hara-Yokoyama et al., Novel sulfated gangliosides, high-affinity ligands for neural siglecs, inhibit NADase activity of leukocyte cell surface antigen CD38, Med. Chem. Lett., 13:3441-3445 (2003).
Hedbys et al., Synthesis of Gal beta 1-3GlcNAc and Gal beta 1-3GlcNAc beta-SEt by an enzymatic method comprising the sequential use of beta-galactosidases from bovine testes and *Escherichia coli*, Glycoconjugate J., 6:161-168 (1989).
Hossain et al., Synthesis and Th1-immunostimulatory activity of a-galactosylceramide analogues bearing a halogen-containing or selenium-containing acyl chain, Bioorg. Med. Chem., 24:3687-3695 (2016).
Inokuchi, GM3 and diabetes, Glycoconj. J., 31:193-197 (2014).
International Application No. PCT/US20/51172, International Search Report and Written Opinion, mailed Dec. 3, 2020.
International Application No. PCT/US2020/051172, International Preliminary Report on Patentability, mailed Mar. 31, 2022.
Ito et al., A novel strategy for synthesis of ganglioside GM3 using an enzymically produced sialoside glycosyl donor, J. Am. Chem. Soc., 115:1603-1605 (1993).
Ito et al., Systematic synthesis and MAG-binding activity of novel sulfated GM1 b analogues as mimics of Chol-1 (alpha-series) gangliosides: highly active ligands for neural siglecs, Carbohydr. Res., 338:1621-1639 (2003).
Iwabuchi et al., Membrane microdomains in immunity: Glycosphingolipid-enriched domain-mediated innate immune responses, BioFactors, 38:275-283 (2012).
Iwayama et al., A First Total Synthesis of Ganglioside HLG-2, Chem. Eur. J., 15:4637-4648 (2009).
Jacques et al., Chemoenzymatic synthesis of GM3 and GM2 gangliosides containing a truncated ceramide functionalized for glycoconjugate synthesis and solid phase applications, Organic & Biomolecular Chemistry, 4:142-154 (2005).
Janssens et al., Efficient Divergent Synthesis of New Immunostimulant 4?-Modified a-Galactosylceramide Analogues, ACS Med. Chem. Lett., 8:642-647 (2017).
Jernigana et al., Sphingolipids in Major Depression , Neurosignals, 23:49-58 (2015).
Kaida et al., Antiganglioside antibodies and their pathophysiological effects on Guillain-Barré syndrome and related disorders—A review, Glycobiology, 19:676-692 (2009).
Kanaya et al., Synthetic studies on glycosphingolipids from protostomia phyla: synthesis of glycosphingolipids and related carbohydrate moieties from the parasite *Schistosoma mansoni*, Carbohydr. Res., 361:55-72 (2012).
Kanaya et al., Synthetic Studies on Glycosphingolipids from Protostomia Phyla: Synthesis of Glycosphingolipids from the Parasite *Schistosoma mansoni*, Chem. Pharm. Bull., 58:811-817 (2010).
Kavaliauskiene et al., Protection against shiga toxins, Toxins, 9:44 (2017).
Kimura et al., A Novel Synthetic Route to a-Galactosyl Ceramides and iGb3 Using DTBS-Directed a-Selective Galactosylation, Synlett, 2379-2382 (2006).
Kinjo et al., Natural Sphingomonas Glycolipids Vary Greatly in Their Ability to Activate Natural Killer T Cells, Chem. Biol., 15:654-664 (2008).
Kolter, Ganglioside biochemistry, ISRN Biochem., 2012:ID 506160 (2012).
Komba et al., 6-O-Sulfo De-N-Acetylsialyl Lewis X as a Novel High-Affinity Ligand for Human L-Selectin: Total Synthesis and Structural Characterization, Biol. Chem., 382:233-240 (2001).
Komori et al., A first total synthesis of a novel sulfated ganglioside, 3'-O-sulfo-GM1b, Carbohydr. Res., 337:1679-1686 (2002).
Komori et al., Design and efficient synthesis of novel GM2 analogues with respect to the elucidation of the function of GM2 activator, Glycoconjugatec J., 25:647-661 (2008).
Kurosu et al., Ganglioside GM3 derivatives with truncated ceramide moiety: facial synthesis and inhibitory activity against KB cell growth, J. Carbohydr. Chem., 25:427-439 (2006).
Lahiri et al., The metabolism and function of sphingolipids and glycosphingolipids, Cell. Mol. Life Sci., 64:2270-2284 (2007).
Langeveld et al., Glycosphingolipids and insulin resistance, Prog. Lipid Res., 48:196-205 (2009).
Lee et al., Total Synthesis of Agelagalastatin, Org. Lett., 8:3971-3974 (2006).
Liu et al., A General Chemoenzymic Strategy for the Synthesis of Glycosphingolipids, Eur. J. Org. Chem., 2016:4315-4320 (2016).
Liu et al., Rapid access to 6"-functionalized a-galactosyl ceramides by using 2-naphthylmethyl ether as the permanent protecting group, Bioorg. Med. Chem. Lett., 27:1795-1798 (2017).
Long et al., Synthesis and evaluation of stimulatory properties of Sphingomonadaceae glycolipid, Nat. Chem. Biol., 3:559-564 (2007).
Lopez et al., Gangliosides in cell recognition and membrane protein regulation, Curr. Opin. Struct. Biol., 19:549-557 (2009).
Luo et al., First synthesis of two deoxy Lewisx pentaosyl glycosphingolipids, Glycoconjugate J., 25:335-344 (2008).
Meek et al., Catalytic Z-selective olefin cross-metathesis for natural product synthesis, Nature, 471:461-466 (2011).
Merrill, Sphingolipid and glycosphingolipid metabolic pathways in the era of sphingolipidomics, Chem. Rev., 111:6387-6422 (2011).
Morales et al., Glycosphingolipids and mitochondria: Role in apoptosis and disease, Gfycoconj. J., 20, 579-588, (2004).
Morales-Serna et al., Recent advances in the glycosylation of sphingosines and ceramides, Carbohydr. Res., 342:1595-1612 (2007).
Mori et al., Synthesis of (4E,8E,2S,3R,2'R-N-2'-hydroxyhexadecanoyl-1-O-Beta-D-glucopyranosyl-9-methyl-4,8-sphingadienine, the fruiting-inducing cerebroside in a basidiomycete Schizophyllum commune, Tetrahedron, 41:2379-2386 (1985).
Mori et al., Synthesis of sphingosine relatives, VII. Synthesis of anti-ulcerogenic cerebrosides isolated from Tetragonia tetragonoides, Liebigs Ann. Chem., 1988:807-814 (1988).
Nakagawa et al., Total synthesis and determination of absolute configuration of cerebroside B1b and its stereoisomers, Tetrahedron Lett., 28:6281-6284 (1987).

(56) References Cited

OTHER PUBLICATIONS

Nakashima et al., A First Total Synthesis of a Hybrid-Type Ganglioside Associated with Amyotrophic Lateral Sclerosis-Like Disorder, Chem. Eur. J., 17:588-597 (2011).
Ng et al., Human genetic disorders involving glycosylphosphatidylinositol (GPI) anchors and glycosphingolipids (GSL), J. Inherit. Metab. Dis., 38:171-178 (2015).
Nicolaou et al., Total synthesis of the tumor-associated Lex family of glycosphingolipids, J. Am. Chem. Soc., 112:3693-3695 (1990).
Nishimura et al., Transfer of Ganglioside GM3 Oligosaccharide from a Water Soluble Polymer to Ceramide by Ceramide Glycanase. A Novel Approach for the Chemical-Enzymatic Synthesis of Glycosphingolipids, J. Am. Chem. Soc., 119:10555-10556 (1997).
Ohashi et al., Syntheses of D-erythro-1-deoxydihydroceramide-1-sulfonic acid and phosphonosphingoglycolipid found in marine organisms via a common precursor, Tetrahedron, 45:2557-2570 (1989).
Ohashi et al., Synthesis of phosphonosphingoglycolipid found in marine snail turbo cornutus, Tetrahedron Lett., 29:1189-1192 (1988).
Ohlsson et al., Analogues of Glycosphingolipids and Glycerolipids Suitable for Conjugation to Gold- and Amino-Functionalised Surfaces, Tetrahedron, 56:9975-9984 (2000).
Ohtsuka et al., Synthesis of a new glycosphingolipid from the marine ascidian Microcosmus sulcatus using a one-pot glycosylation strategy, Tetrahedron, 69:1470-1475 (2013).
Ohtsuka et al., Synthesis of a new glycosphingolipid, neurosporaside, from Neurospora crassa, Carbohydr. Res., 404:9-16 (2015).
Ohtsuka et al., Synthetic studies on glycosphingolipids from the Protostomia phyla: syntheses of arthro-series glycosphingolipids, Carbohydr. Res., 337:2037-2047 (2002).
Palmano et al., The Role of Gangliosides in Neurodevelopment, Nutrients, 7:3891-3913 (2015).
Pilgrim et al., Synthesis of a-O- and a-S-glycosphingolipids related to Sphingomonous cell wall antigens using anomerisation, Molecules, 18:11198-11218 (2013).
Prokazova et al., Gangliosides and atherosclerosis, Lipids, 29:1-5 (1994).
Qamsari et al., Ganglioside as a therapy target in various types of cancer, Asian Pac. J. Cancer Prev., 17:1643-1647 (2016).
Qiu et al., Gal(1-3)GalNAc block donor for the synthesis of TF and a Sialy(2-6)TF as glycopeptide building blocks, Tetrahedron Lett., 37:595-598 (1996).
Rich et al., A Chemoenzymatic Total Synthesis of the Neurogenic Starfish Ganglioside LLG-3 Using an Engineered and Evolved Synthase, Angew. Chem., Int. Ed., 51:8640-8643 (2012).
Rich et al., Glycosphingolipid synthesis employing a combination of recombinant glycosyltransferases and an endoglycoceramidase glycosynthase, Chem. Commun., 47:10806-10808 (2011).
Rich et al., S-Linked Ganglioside Analogs for Use in Conjugate Vaccines, Org. Lett., 6:897-900 (2004).
Russo et al., Glycosphingolipid-Protein Interaction in Signal Transduction, Int. J. Mol. Sci., 17:1732 (2016).
Sanchez-Fernandez et al., Glycomimetic-based pharmacological chaperones for lysosomal storage disorders: lessons from Gaucher, GM1-gangliosidosis and Fabry diseases, Chem. Commun., 52:5497-5515 (2016).
Sandbhor et al., Substrate Recognition of the Membrane-Associated Sialidase NEU3 Requires a Hydrophobic Aglycone, Biochemistry, 50:6753-6762 (2011).
Sandhoff et al., Gangliosides and Gangliosidoses: Principles of Molecular and Metabolic Pathogenesis, J. Neurosci., 33:10195-10208 (2013).
Sato et al., Stereo- and regio-controlled, total synthesis of the Leb antigen, III4 FucIV2FucLcOSe4 Cer, Carbohydr. Res., 155:C1-C5 (1986).
Sawant et al., An unusual Wittig reaction with sugar derivatives: exclusive formation of a 4-deoxy analogue of a-galactosyl ceramide, RSC Adv., 4:26524-26534 (2014).
Schengrund, Gangliosides: glycosphingolipids essential for normal neural development and function, Trend. Biochem. Sci., 40:397-406 (2015).
Schmidt et al., Short synthesis of cerebrosides, Angew. Chem., 97:60-61 (1985).
Schnaar, Gangliosides of the Vertebrate Nervous System, J. Mol. Biol., 428:3325-3336 (2016).
Schuette et al., Influence of Gb3 glycosphingolipids differing in their fatty acid chain on the phase behaviour of solid supported membranes: chemical syntheses and impact of Shiga toxin binding. Chem. Sci., 5:3104-3114 (2014).
Shiozaki et al., Synthesis of RCAI-172 (C6 epimer of RCAI-147) and its biological activity, Bioorg. Med. Chem., 22:827-833 (2014).
Singh et al., Synthesis of a (4E, 8Z)-Sphingadienine Moiety Containing Cerebroside from Tetragonia Tetragonoides with Antiulcerogenic Activity1,2, J. Carbohydr. Chem., 8:199-216 (1989).
Smith et al., Glycosphingolipids as toxin receptors, Semin. Cell Dev. Biol., 15:397-408 (2004).
Stults et al., Glycosphingolipids: Structure, Biological Source, and Properties, Method. Enzym., 179:167-214 (1989).
Takeda et al., Synthesis of a-series ganglioside GM1a containing C20-sphingosine, Carbohydr. Res., 340:211-220 (2005).
Tanaka et al., 1,2-cis-a-Stereoselective Glycosylation Utilizing a Glycosyl-Acceptor-Derived Borinic Ester and Its Application to the Total Synthesis of Natural Glycosphingolipids, Org. Lett., 18:5030-5033 (2016).
Thompson et al., Organization of glycosphingolipids in bilayers and plasma membranes of mammalian cells, Annu. Rev. Biophys. Biophys. Chem., 14:361-386 (1985).
Thon et al., PmST2: a novel Pasteurella multocida glycolipid a2-3-sialyltransferase, Glycobiology, 21:1206-1216 (2011).
Tietze et al., Synthesis of a novel ether-bridged GM3-lactone analogue as a target for an antibody-based cancer therapy, Chem. Eur. J., 6:2801-2808 (2000).
Todeschini et al., Functional role of glycosphingolipids and gangliosides in control of cell adhesion, motility, and growth, through glycosynaptic microdomains, Biochim. Biophys. Acta., 1780:421-433 (2008).
Vankar et al., Chemistry of glycosphingolipids—carbohydrate molecules of biological significance, Chem. Soc. Rev., 29:201-216 (2000).
Vaughan et al., Glycosynthase-mediated synthesis of glycosphingolipids, J. Am. Chem. Soc., 128:6300-6301 (2006).
Viard et al., The role of glycosphingolipids in HIV signaling, entry and pathogenesis, Glycoconj. J., 20:213-222 (2004).
Wennekes et al., Glycosphingolipids—Nature, Function, and Pharmacological Modulation, Angew. Chem. Int. Ed., 48:8848-8869 (2009).
Wisse et al., Synthesis of a Panel of Carbon-13-Labelled (Glyco)Sphingolipids, European Journal of Organic Chemistry, 2015:2661-2677 (2015).
Xia et al., Modification of the Ceramide Moiety of Isoglobotrihexosylceramide on Its Agonist Activity in Stimulation of Invariant Natural Killer T Cells, J. Med. Chem., 50:3489-3496 (2007).
Xia et al., Synthesis and biological evaluation of alpha-galactosylceramide (KRN7000) and isoglobotrihexosylceramide (iGb3), Bioorg. Med. Chem. Lett., 16:2195-2199 (2006).
Xia et al., Thio-isoglobotrihexosylceramide, an Agonist for Activating Invariant Natural Killer T Cells, Org. Lett., 8:5493-5496 (2006).
Xing et al., Facile Synthesis of Tumor-Associated Carbohydrate Antigen Ganglioside GM3 from Sialic Acid, Lactose, and Serine, Eur. J. Org. Chem., 2009:5963-5970 (2009).
Xu et al., Multi-system disorders of glycosphingolipid and ganglioside metabolism, J. Lipid Res., 51:1643-1675 (2010).
Yamaguchi et al., Studies on the endogenous L-selectin ligands: systematic and highly efficient total synthetic routes to lactamized-sialyl 6-O-sulfo Lewis X and other novel gangliosides containing lactamized neuraminic acid, Carbohydr. Res., 338:2793-2812 (2003).
Yamaguchi et al., Synthesis and selectin-binding activity of N-deacetylsialyl Lewis X ganglioside, Carbohydr. Res., 337:2111-2117 (2002).

(56) References Cited

OTHER PUBLICATIONS

Yamaguchi et al., Total synthesis of 6-O-sulfo-sialylparagloboside: a widely useful glycoprobe for biochemical research, Carbohydr. Res., 343:1849-1857 (2008).
Yamamura et al., Synthetic studies on glycosphingolipids from Protostomia phyla: total syntheses of glycosphingolipids from the parasite, *Echinococcus multilocularis*, Carbohydr. Res., 339:2749-2759 (2004).
Yang et al., A FRET Probe for Cell-Based Imaging of Ganglioside-Processing Enzyme Activity and High-Throughput Screening, Angew. Chem., Int. Ed., 54:5389-5393 (2015).
Yen et al., Concise Syntheses of a-Galactosyl Ceramide, d-ribo-Phytosphingosine, and Ceramide, Synthesis, 45:511-517 (2013).
Yin et al., Alpha Anomers of iGb3 and Gb3 Stimulate Cytokine Production by Natural Killer T Cells, ACS Chem. Biol., 4:191-197 (2009).
Yu et al., Streamlined chemoenzymatic total synthesis of prioritized ganglioside cancer antigens, Organic & Biomolecular Chemistry, 16:4076-4080 (2018).
Yu et al., Structures, biosynthesis, and functions of gangliosides—An overview, J. Oleo. Sci., 60:537-544 (2011).
Zhang et al., Glycosphingolipids in health and disease, Annu. Clin. Lab. Sci., 34:3-13 (2004).
Zhang et al., Study of carbohydrate carbohydrate interactions: total synthesis of 6d-deoxy Lewisx pentaosyl glycosphingolipid, Tetrahedron, 66:7373-7383 (2010).
Zheng et al., Synthesis of N-modified ganglioside GM3 derivatives, Tetrahedron, 68:1475-1482 (2012).
Zimmermann et al., Azidosphingosine Glycosylation in Glycosphingolipid Synthesis, J. Carbohydr. Chem., 7:435-452 (1988).

* cited by examiner

SYNTHESIS OF GLYCOSPHINGOLIPIDS

CROSS-REFERENCE TO RELATED APPLICATIONS

This application claims the benefit of priority of U.S. Provisional Patent Application No. 62/901,609, filed Sep. 17, 2019, the disclosure of which is hereby incorporated by reference in its entirety.

STATEMENT OF GOVERNMENT SUPPORT

This invention was made with government support under Grant No. 1800279, awarded by the National Science Foundation. The government has certain rights in the invention.

FIELD OF THE DISCLOSURE

The disclosure relates generally to glycolipids and methods of preparing same. More specifically, the disclosure relates to glycosphingolipds and methods of preparing same.

BACKGROUND

Glycosphingolipids (GSLs) are a family of glycolipids with a ceramide as the lipid linked to the reducing end of a glycan. GSLs are a major and essential component of the cell membrane. For example, in a vertebrate brain, 80% of glycoconjugates are glycolipids. GSLs play an important role in many biological processes and are related to many diseases such as cancer, bacterial and viral infection, diabetes, sclerosis, Alzheimer's disease, lysosomal storage disorders (e.g., Gaucher disease and Fabry disease), and the like.

However, GSLs are very difficult to access. GSLs can be obtained from nature only in very minor quantity and heterogeneous forms and chemical or enzymatic syntheses suffer from low yields and/or compatibility problems and, most importantly, provide only individual structures one by one.

SUMMARY

One aspect of the disclosure provides a method of synthesizing a glycolipid of Formula (I):

(I)

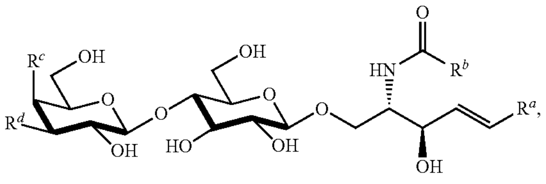

wherein $R^a$ is a $C_{1-30}$alkylene-A; $R^b$ is $C_{1-30}$alkylene-A′ A and A′ are independently H, a fluorescent or molecular tag, or $N_3$; each of $R^c$ and $R^d$ independently comprise OH or a monosaccharide, disaccharide, trisaccharide, or tetrasaccharide; the method including (a) admixing a glycan intermediate of Formula (II) with an alkene CH═CH—$R^a$ in the presence of Grubbs II catalyst to form an alkene intermediate of Formula (III):

(II)

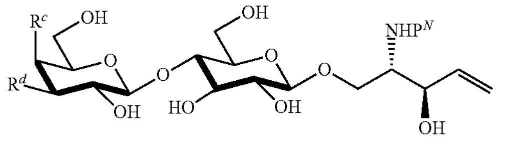

and (III)

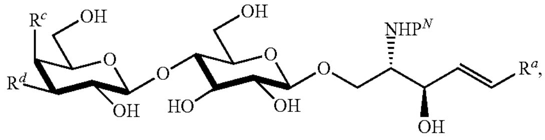

wherein $P^N$ is Boc, Fmoc, Cbz, or Troc, $HP^N$ together form Phth, or $NHP^N$ together form $N_3$; (b) deprotecting the alkene intermediate of Formula (III) to form a deprotected amine, and (c) reacting the deprotected amine with Cl—C(O)$R^b$, $R^b$C(O)—O—C(O)$R^b$, or HO—C(O)$R^b$ to form the glycolipid of Formula (I).

Another aspect of the disclosure provides a glycan intermediate of Formula (II):

(II)

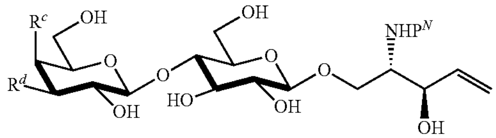

, wherein each of $R^c$ and $R^d$ independently comprise OH or a monosaccharide, disaccharide, trisaccharide, or tetrasaccharide; and $P^N$ is Boc, Fmoc, Cbz, or Troc, $HP^N$ together form Phth, or $NHP^N$ together form $N_3$. In embodiments, the glycan intermediate of Formula (II) is prepared by forming an appropriate monosaccharide, disaccharide, trisaccharide, or tetrasaccharide chain independently and sequentially through step-by-step regio- and stereoselective enzymatic glycosylation of a precursor having a structure of compound (1), using sugar-nucleotides as glycosyl donors in the presence of glycosyltransferases to insert the saccharide moiety(ies) at $R^c$ and/or $R^d$ (1)

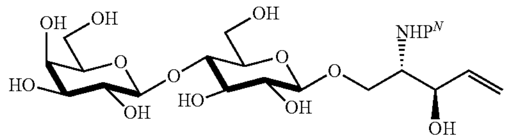

wherein $P^N$ is Boc, Fmoc, Cbz, or Troc, $HP^N$ together form Phth, or $NHP^N$ together form $N_3$.

Another aspect of the disclosure provides an alkene intermediate of Formula (IV):

(IV)

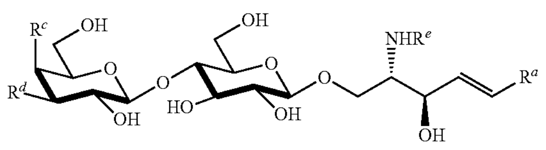

wherein $R^a$ is a $C_{1-30}$alkyl; each of $R^c$ and $R^d$ independently comprise OH or a monosaccharide, a disaccharide, trisaccharide, or tetrasaccharide; and $R^e$ is H or Boc, Fmoc, Cbz, or Troc, $HP^N$ together form Phth, or $NHP^N$ together form $N_3$.

The foregoing summary is not intended to define every aspect of the disclosure, and additional aspects are described in other sections, such as the Detailed Description and Examples. The entire document is intended to be related as a unified disclosure, and it should be understood that all combinations of features described herein are contemplated, even if the combination of features are not found together in the same sentence, or paragraph, or section of this document.

In addition to the foregoing, the disclosure includes, as an additional aspect, all embodiments of the disclosure narrower in scope in any way than the variations specifically mentioned above. If aspects of the disclosure are described as "comprising" a feature, embodiments are also contemplated "consisting of" or "consisting essentially of" the feature.

DETAILED DESCRIPTION

Many modifications and other embodiments will come to mind to one skilled in the art to which the disclosed compositions and methods pertain having the benefit of the teachings presented herein. Therefore, it is to be understood that the disclosures are not to be limited to the specific embodiments disclosed and that modifications and other embodiments are intended to be included within the scope of the appended claims.

Disclosed herein are methods of synthesizing a glycolipid of Formula (I):

(I)

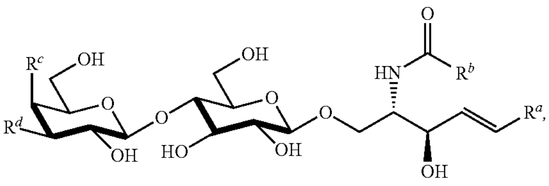

wherein $R^a$ is a $C_{1-30}$alkylene-A; $R^b$ is $C_{1-30}$alkylene-A□A and A□a re independently H, a fluorescent or molecular tag, or $N_3$; each of $R^c$ and $R^d$ independently comprise OH or a monosaccharide, disaccharide, trisaccharide, or tetrasaccharide; the method including (a) admixing a glycan intermediate of Formula (II) with an alkene CH═CH—$R^a$ in the presence of Grubbs II catalyst to form an alkene intermediate of Formula (III):

(II)

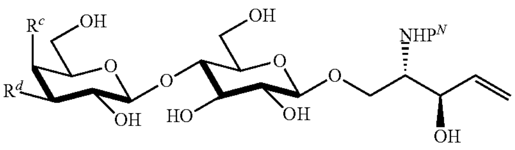

and (III)

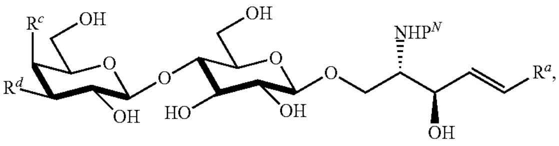

wherein $P^N$ is t-butyl carbamate (Boc), 9-fluorenylmethyl carbamate (Fmoc), benzyl carbamate (Cbz), or 2,2,2-Trichloroethoxycarbonyl (Troc), $HP^N$ together form a phthalimide (Phth), or $NHP^N$ together form azido ($N_3$);

(b) deprotecting the alkene intermediate of Formula (III) to form a deprotected amine, and (c) reacting the deprotected amine with Cl—C(O)$R^b$, $R^b$C(O)—O—C(O)$R^b$, or HO—C(O)$R^b$ to form the glycolipid of Formula (I).

In general, $R^a$ is a $C_{1-30}$alkylene-A. As used herein, and unless specified otherwise, the term "alkyl" refers to straight or branched chain hydrocarbyl groups including from 1 to 30 carbon atoms. For instance, an alkyl can have from 1 to 20 carbon atoms, 2 to 20 carbon atoms, 3 to 15 carbon atoms, or 4 to 13 carbon atoms. The term $C_n$ means that the alkyl group has "n" carbon atoms. For example, $C_4$alkyl refers to an alkyl group that has 4 carbon atoms. $C_{4-14}$alkyl refers to an alkyl group having a number of carbon atoms encompassing the entire range (i.e., 4 to 13 carbon atoms), as well as all subgroups (e.g., 4-12, 4-11, 4-10, 5-9, 6-8, 4, 5, 6, 7, 8, 9, 10, 11, 12, and 13 carbon atoms). Exemplary alkyls include straight chain alkyl groups such as butyl, pentyl, hexyl, heptyl, octyl, nonyl, decyl, undecyl, dodecyl, tridecyl, tetradecyl, and the like, and also include branched chain isomers of straight chain alkyl groups. Thus, alkyl groups include primary alkyl groups, secondary alkyl groups, and tertiary alkyl groups. As used herein, and unless specified otherwise, "alkylene" refers to an alkyl group having a further substituent. For example, the term "alkylene-A" refers to an alkyl group substituted with an "A" group.

In embodiments, $R^a$ is a $C_{1-30}$alkylene-A. In embodiments, $R^a$ is $C_{1-20}$alkylene-A. In embodiments, $R^a$ is a $C_{2-18}$alkylene-A. In embodiments, $R^a$ is a $C_{4-15}$alkylene-A. In embodiments, $R^a$ is a $C_{4-13}$alkylene-A. In embodiments, $R^a$ is a $C_{9-15}$alkylene-A. In embodiments, $R^a$ is a $C_{10-14}$alkylene-A. In embodiments, $R^a$ is a $C_{11-13}$alkylene-A. In embodiments, $R^a$ is a $C_{11}$alkylene-A. In embodiments, $R^a$ is a $C_{13}$alkylene-A. In embodiments, $R^a$ is a $C_4$alkylene-A. In general, A is H or a fluorescent or molecular tag or $N_3$. In embodiments, A is H. In embodiments, A is a fluorescent tag. In embodiments, A is a molecular tag. In embodiments, A is $N_3$. In embodiments, $R^a$ is a $C_{2-18}$alkylene-A and A is H. In embodiments, $R^a$ is a $C_{2-18}$alkylene-A and A is a fluorescent tag. In embodiments, $R^a$ is a $C_{2-18}$alkylene-A and A is a molecular tag. In embodiments, $R^a$ is a $C_{11}$alkylene-A and A is H. In embodiments, $R^a$ is a $C_{11}$alkylene-A and A is fluorescent tag. In embodiments, $R^a$ is a $C_{11}$alkylene-A and A is a molecular tag. In embodiments, $R^a$ is a $C_{13}$alkylene-A and A is H. In embodiments, $R^a$ is a $C_{13}$alkylene-A and A is fluorescent tag. In embodiments, $R^a$ is a $C_{13}$alkylene-A and A is a molecular tag. In embodiments, $R^a$ is a $C_{2-18}$alkylene-A and A is $N_3$. In embodiments, $R^a$ is a $C_{11}$alkylene-A and A is $N_3$. In embodiments, $R^a$ is a $C_{13}$alkylene-A and A is $N_3$. In embodiments, $R^a$ is a $C_4$alkylene-A and A is H.

In general, $R^b$ is a $C_{1-30}$alkylene-A□ In embodiments, $R^b$ is $C_{1-30}$alkylene-A□ In embodiments, $R^b$ is $C_{1-20}$alkylene-A□ In embodiments, $R^b$ is $C_{2-18}$alkylene-A□ In embodiments, $R^b$ is $C_{2-17}$alkylene-A□ In embodiments, $R^b$ is $C_{17}$alkylene-A□ In embodiments, $R^b$ is $C_{10}$alkylene-A□ In general, A□s H or a fluorescent or molecular tag or $N_3$. In embodiments, A□s H. In embodiments, A□s a fluorescent tag. In embodiments, A□s a molecular tag. In embodiments, A□s $N_3$. In embodiments, $R^b$ is a $C_{2-17}$alkylene-A □a nd A□ is H. In embodiments, $R^b$ is a $C_{2-17}$alkylene-A □a nd A□s a fluorescent tag. In embodiments, $R^b$ is a $C_{2-17}$alkylene-A □a nd A□s a molecular tag. In embodiments, $R^b$ is a $C_{17}$alkylene-A□ and A□s H. In embodiments, $R^b$ is a $C_{17}$alkylene-A □a nd A□s fluorescent tag. In embodiments, $R^b$ is a $C_{17}$alkylene-A □a nd A□s a molecular tag. In embodiments, $R^b$ is a $C_{10}$alkylene-A □a nd A□s H. In embodiments, $R^b$ is a $C_{10}$alkylene-A □a nd A□s fluorescent tag. In embodiments, $R^b$ is a $C_{10}$alkylene-A □a nd A□s a molecular tag. In embodiments, $R^b$ is a $C_{2-17}$alkylene-A □a nd A□s $N_3$. In embodiments, $R^b$ is a $C_{17}$alkylene-A □a nd A□s $N_3$. In embodiments, $R^b$ is a $C_{10}$alkylene-A □a nd A□s $N_3$. In embodiments, $R^b$ is a $C_1$alkylene-A□ and A□s $N_3$.

The fluorescent tag can generally be any fluorescent tag known in the art. In embodiments, the fluorescent tag is a fluorophore. In embodiments, the fluorescent tag comprises nitrobenzoxadiazole (NBD), 4,4-difluoro-4-bora-3a,4a-diaza-s-indacene (BODIPY), substituted BODIPY, pyrene, dansyl, fluorescein (FITC), or octatetraene. In embodiments, the fluorescent tag comprises NBD. As shown in Examples 13 and 14, nitrobenzoxadiazole (NBD)-labeled glycolipids can be prepared using the methods of the disclosure.

The molecular tag can generally be any molecular tag known in the art. Exemplary molecular tags include, but are not limited to, spin labels, affinity tags, and functional groups useful for imparting further functionality. For example, as shown in Example 12, the GSL compound can include an azido ($N_3$) group. Through the azido group, other functionality can be attached to the lipid by click chemistry (reaction of the azido with an alkyne with desired functionality), as is well known in the art. The azido group can be used to introduce a molecular tag or fluorescent tag via an alkyne molecular tag or alkyne fluorescent tag. For example, dibenzocyclooctyne (DBCO) with a fluorescent tag such as CY3 or CY5, or molecular tag such as $PEG_4$-dUTP can be reacted with an azido group in copper-free conditions of biological systems. Terminal alkynes with fluorescent tags or molecular tags can be reaction with an azido group in the presence of copper(I) catalysts before introduction to a biological system.

In general, each of $R^c$ and $R^d$ independently comprise OH or a monosaccharide, disaccharide, trisaccharide, or tetrasaccharide. In embodiments, one of $R^c$ and $R^d$ are OH. In embodiments, both $R^c$ and $R^d$ are OH. In embodiments, one of $R^c$ and $R^d$ is a monosaccharide. In embodiments, both of $R^c$ and $R^d$ are a monosaccharide. In embodiments, one of $R^c$ and $R^d$ is a disaccharide. In embodiments, both of $R^c$ and $R^d$ are a disaccharide. In embodiments wherein both $R^c$ and $R^d$ are a monosaccharide, disaccharide, trisaccharide, or tetrasaccharide, $R^c$ and $R^d$ can be the same saccharide(s) or different saccharides. In embodiments, $R^c$ is a monosaccharide, disaccharide, trisaccharide, or tetrasaccharide and $R^d$ is OH. In embodiments, $R^c$ is a monosaccharide or a disaccharide and $R^d$ is OH. In embodiments, $R^c$ is OH and $R^d$ is a monosaccharide, disaccharide, trisaccharide, or tetrasaccharide. In embodiments, $R^c$ is OH and $R^d$ is a monosaccharide or a disaccharide. The saccharides are not particularly limited and can be any natural or unnatural saccharide. In embodiments, the monosaccharide is selected from the group consisting of sialic acid, galactose, and galactosamine. In embodiments, the monosaccharide, disaccharide, trisaccharide, or tetrasaccharide of at least one of $R^c$ and $R^d$ is selected from the group consisting of sialic acid, galactose, and galactosamine. In embodiments, $R^c$ is OH and $R^d$ is sialic acid. In embodiments, $R^d$ is OH and $R^c$ is galactose or galactosamine. In embodiments, the disaccharide, trisaccharide, or tetrasaccharide comprises a monosaccharide selected from the group consisting of sialic acid, galactose, and galactosamine.

In general, $P^N$ can be any amino protecting group known in the art. For example, suitable amino protecting groups can include, but are not limited to, phthalimides, amides, azido, and carbamate protecting groups. In embodiments, $P^N$ comprises a carbamate protecting group. In embodiments, $P^N$ is selected from the group consisting of Boc, Fmoc, Cbz, and Troc. In embodiments, $P^N$ is Boc. In embodiments, $P^N$ is Fmoc. In embodiments, $P^N$ is Cbz. In embodiments, the protecting group can be bidentate such that the protecting group is bonded to the N in the —$NHP^N$ moiety in place of the H. Suitable bidentate protecting groups include, but are not limited to, phthalimides. In embodiments, $HP^N$ together form Phth. In embodiments, the protecting group be in place of the —$NHP^N$ moiety, for example, an $N_3$ group. In embodiments, $NHP^N$ together form $N_3$.

The methods of the disclosure provide rapid assembly of various GSLs and GSL derivatives and analogs and are advantageous over known methods for one or more reasons, such as improved yield for short lipid glycosylation, water-soluble substrates for enzymatic carbohydrate synthesis, efficient construction of the ceramide moiety, and/or diversity-oriented synthesis of various GSLs and derivatives. In this respect, compound (1) is a universal starting point for preparing a variety of GSL compounds with unlimited lipid chains and saccharide modifications. Compound (1)

(1)

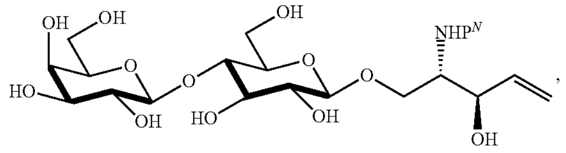

wherein $P^N$ is Boc, Fmoc, Cbz, or Troc, $HP^N$ together form Phth, or $NHP^N$ together form $N_3$, is designed as the versatile core to be decorated on both glycan and lipid sides. On the glycan side, most of the glycosphingolipids (GSLs) have a lactose as the starting point for biosynthesis. Elongation of the lactose unit gives access to glycans of all glycosphingolipids. On the other side are the lipids, which contribute to the heterogeneity of the GSLs and affect their localization on cell surfaces. By modifying the lipid chains, desired functionalities can be easily accessed. The lipid chains can be elongated as described herein, using different length lipid chains as well as functionalized lipid chains to provide derivative GSLs.

In general, in the methods of the disclosure, the admixing in step (a) of the a glycan intermediate of Formula (II) with an alkene CH═CH—$R^a$ in the presence of Grubbs II catalyst to form the alkene intermediate of Formula (III) can be under any conditions sufficient to form the alkene intermediate of Formula (III). As used herein, Grubbs II catalysts refer to olefin metathesis catalysts such as [1,3-bis(2,4,6-trimethylphenyl)-2-imidazolidinylidene]dichloro(phenylmethylene)(tricycloyhelxylphosphine)ruthenium dichloride and [1,3-bis(2,4,6-trimethylphenyl)-2-imidazolidinylidene]dichloro(o-isopropoxyphenylmethylene)ruthenium.

In embodiments, the conditions sufficient to form the alkene intermediate of Formula (III) include reacting the glycan intermediate of Formula (II) and the alkene CH═CH—$R^a$, optionally in the presence of a solvent. The solvent can be any solvent known in the art as sufficient for use in Grubbs II catalyst-promoted olefin metathesis. In embodiments, the solvent comprises a polar solvent. In embodiments, the solvent comprises dichloromethane, acetic acid, methanol, dimethylformamide, or a combination thereof. In embodiments, the solvent comprises dichloromethane, acetic acid, or a combination thereof. In embodiments, the solvent comprises a combination of dichloromethane and acetic acid. In embodiments, the solvent comprises a combination of dichloromethane and acetic acid in a volume ratio of about 3:1 to about 1:3, about 2:1 to about 1:2, about 1.5:1 to about 1:1.5, about 1:1 to about 1:2, about 1:1 to about 1:3, for example, about 3:1, about 2:1, about 1:1, about 1:2, or about 1:3. In embodiments, dichloromethane and acetic acid can be provided in a volume ratio of about 1:1 to about 1:3. In embodiments, dichloromethane and acetic acid can be provided in a volume ratio of about 1:1.

In general, the conditions sufficient to form the alkene intermediate of Formula (III) include the presence of about 3 mol %, about 5 mol %, about 10 mol %, about 15 mol %, about 20 mol %, about 25 mol %, about 30 mol %, about 35 mol %, about 40 mol %, about 45 mol %, or about 50 mol % of the Grubbs II catalyst, for example, in a range of about 1 mol % to about 50 mol %, about 10 mol % to about 50 mol %, about 20 mol % to about 40 mol %, or about 25 mol % to about 35 mol %. In embodiments, the Grubbs II catalyst is present in about 25 mol % to about 35 mol %.

In general, conditions sufficient to form the alkene intermediate of Formula (III) include reacting the glycan intermediate of Formula (II) with a molar excess of the alkene CH═CH—$R^a$. In embodiments, the alkene is provided in about 2 molar equivalents to about 20 molar equivalents, about 2 to about 18 molar equivalents, about 4 to about 16 molar equivalents, about 5 to about 15 molar equivalents, about 6 to about 14 molar equivalents, about 8 to about 12 molar equivalents, about 9 to about 11 molar equivalents, or about 10 molar equivalents, relative to the glycan intermediate of Formula (II). In embodiments, the alkene is provided in about 5 to about 15 molar equivalents, relative to the glycan intermediate of Formula (II).

In general, conditions sufficient to form the alkene intermediate of Formula (III) include reacting the glycan intermediate of Formula (II) and the alkene CH═CH—$R^a$ at room temperature (about 23 to 25° C.) for an amount of time sufficient to form the alkene intermediate of Formula (III) in suitable yield. In embodiments, the reaction is stirred for about 1 hour to about 48 hours, for example, about 1 hour, about 5 hours, about 10 hours, about 12 hours, about 18 hours, about 24 hours, about 30 hours, about 36 hours, about 42 hours, or about 48 hours. In embodiments, the reaction is stirred for about 20 hours to about 28 hours, about 22 hours to about 26 hours, about 23 hours to about 25 hours, or about 24 hours. Without intending to be bound by theory, it is believed that after about 24 hours of stirring, the reaction to form the alkene intermediate of Formula (III) has progressed to the point of maximum yield and while additional conversion of the starting material may take place after about 24 hours, no appreciable increase in yield will be obtained due to poisoning of the catalyst by the solvent. Advantageously, any glycan intermediate of Formula (II) that is not converted to the alkene intermediate of Formula (III) can be recovered and reused. Thus, in embodiments, the admixing in step (a) of the a glycan intermediate of Formula (II) with an alkene CH═CH—$R^a$ in the presence of Grubbs II catalyst to form the alkene intermediate of Formula (III) further includes isolation of the alkene intermediate of Formula (III) and/or recovery of unreacted glycan intermediate of Formula (II).

In general, the deprotecting in step (b) of the alkene intermediate of Formula (III) to form a deprotected amine can be under any conditions sufficient to convert the $NHP^N$ moiety to an $NH_2$ moiety. Methods of deprotecting amino groups are well known in the art and can include, but are not limited to, treatment with an acid (e.g., trifluoro acetic acid, an aqueous solution of phosphoric acid, or hydrochloric acid in methanol), and treatment with $ZnBr_2$. In embodiments, the conditions sufficient to convert the $NHP^N$ moiety to an $NH_2$ moiety include admixing the alkene intermediate of Formula (III) with $ZnBr_2$. In embodiments, the admixing of the alkene intermediate of Formula (III) with $ZnBr_2$ is in the presence of a solvent. In embodiments, the solvent comprises a polar solvent. In embodiments, the solvent comprises ethanol, methylene chloride, acetic acid, or a combination thereof. In embodiments, the solvent comprises ethanol.

In general, conditions sufficient to convert the $NHP^N$ moiety to an $NH_2$ moiety can include reacting the alkene intermediate of Formula (III) with $ZnBr_2$ for about 1 hour to about 48 hours, for example, about 1 hour, about 5 hours, about 10 hours, about 12 hours, about 16 hours, about 18 hours, about 24 hours, about 30 hours, about 36 hours, about 42 hours, or about 48 hours. In embodiments, the reaction is stirred for about 8 hours to about 22 hours, about 10 hours to about 20 hours, about 12 hours to about 18 hours, about 14 hours to about 18 hours or about 16 hours. Without intending to be bound by theory, it is believed that after about 16 hours of stirring, the reaction to form the deprotect the alkene intermediate of Formula (III) has progressed to the point of maximum conversion and while additional conversion may take place after about 16 hours, no appreciable increase in yield will be obtained.

In general, the reacting in step (c) of the deprotected amine with Cl—C(O)$R^b$, $R^b$C(O)—O—C(O)$R^b$, or HO—C(O)$R^b$ to form the glycolipid of Formula (I) can be under any conditions sufficient to form the glycolipid of Formula (I). The deprotected amine can be reacted with the fatty acid, fatty ester, or fatty acid chloride in the presence of a base, optionally in the presence of a solvent. In embodiments, the solvent comprises a polar solvent. In embodiments, the solvent comprises methanol, methylene chloride, acetic acid, or a combination thereof. In embodiments, the solvent comprises a combination of methanol and dichloromethane.

In embodiments, the solvent comprises a combination of methanol and dichloromethane in a volume ratio of about 3:1 to about 1:3, about 2:1 to about 1:2, about 1.5:1 to about 1:1.5, about 1:1 to about 1:2, about 1:1 to about 1:3, for example, about 3:1, about 2:1, about 1:1, about 1:2, or about 1:3. In embodiments, methanol and dichloromethane can be provided in a volume ratio of about 1:1 to about 1:3. In embodiments, methanol and dichloromethane can be provided in a volume ratio of about 1:3.

The reacting of step (c) can take place in the presence of a base. In general, any base suitable for amide coupling reactions is suitable. Typically, the base can be a hindered base and poorly nucleophilic such that the base will not compete with the nucleophilic amine in the coupling reaction. In embodiments, the base can include triethylamine, 2,2,6,6-tetramethylpiperidine, N,N-diisopropylethylamine (DIPEA), pyridine, 2,6-lutidine, 4-dimethylaminopyridine, or a combination thereof. In embodiments, the base can include DIPEA.

In general, conditions sufficient to form the glycolipid of Formula (I) can include reacting the deprotected amine with the fatty acid or fatty acid chloride for about 1 hour to about 48 hours, for example, about 1 hour, about 5 hours, about 10 hours, about 12 hours, about 16 hours, about 18 hours, about 24 hours, about 30 hours, about 36 hours, about 42 hours, or about 48 hours. In embodiments, the reaction is stirred for about 8 hours to about 22 hours, about 10 hours to about 20 hours, about 12 hours to about 18 hours, about 14 hours to about 18 hours or about 16 hours. Without intending to be bound by theory, it is believed that after about 16 hours of stirring, the reaction to form the glycolipid of Formula (I) has progressed to the point of complete consumption of the deprotected amine. Consumption of the deprotected amine can be monitored by thin layer chromatography (TLC).

In embodiments wherein at least one of $R^c$ and $R^d$ comprise a monosaccharide, a disaccharide, a trisaccharide or a tetrasaccharide, the method further comprises installing $R^c$ and $R^d$ by reacting a compound (1):

(1)

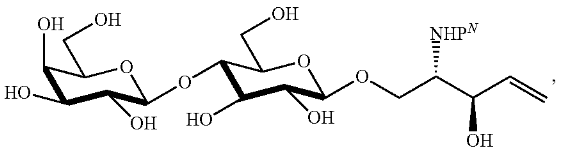

wherein $P^N$ is Boc, Fmoc, or Troc, $HP^N$ together form Phth, or $NHP^N$ together form $N_3$, with a monosaccharide intermediate or iteratively with multiple monosaccharide intermediates, sequentially, under enzymatic elongation conditions to provide the glycan intermediate of Formula (II).

The monosaccharide intermediate can be any natural monosaccharide or a modified derivative in the form of a sugar-nucleotide such that it can be coupled to a hydroxyl group on the glycan moiety, facilitated by an enzyme. Some contemplated examples of the monosaccharide intermediates for enzymatic coupling with a hydroxyl group of a glycan moiety include, but are not limited to, UDP-glucose (UDP-Glc), UDP-galactose (UDP-Gal), UDP-N-acetyl-glucosamine (UDP-GlcNAc), UDP-N-acetyl-galactosamine (UDP-GalNAc), UDP-glucuronic acid (UDP-GlcA), GDP-mannose (GDP-Man), GDP-fucose (GDP-Fuc), CMP-sialic acid (CMP-NANA), and their sugar modified forms, such as 6-azido, 2-N-azidoacyl, and other 6- and 2-N-derivatives of UDP-GlcNAc or UDP-GalNAc, 6-azido and other 6-derivatives of GDP-Fuc, and 9-azido, 5-N-azidoacyl and other 9- and 5-N-derivatives of CMP-NANA. The monosaccharide intermediates can be obtained commercially or can be prepared by enzymatic syntheses using known techniques. Methods of preparing monosaccharide intermediates for enzymatic coupling with a hydroxyl group of a glycan moiety are known in the art. In embodiments, the monosaccharide intermediate is prepared by a method including reacting a sialic acid with cytidine triphosphate (CTP) in the presence of CMP-sialic acid synthase (NmCSS). In embodiments, the monosaccharide intermediate is prepared by a method including reacting uridine triphosphate (UTP) with glucose-1-P, galactose-1-P, N-acetyl-glucosamine-1-P, N- or acetyl-galactosamine-1-P, or by reacting guanosine triphosphate (GTP) with mannose-1-P or fucose-1-P. In embodiments, the monosaccharide intermediate is prepared by a method comprising reacting a monosaccharide-1-phosphate with CTP, UTP, or GTP in the presence of a sugar-nucleotide synthase, such as NmCSS.

In general, enzymatic elongation conditions include consecutive addition of monosaccharides to the glycan moiety facilitated by an enzyme, for example, as disclosed by the Chen and Wang groups in Org. Biomol. Chem., 2016, 2809 and references therein, herein incorporated by reference in their entirety. In embodiments, the enzymatic elongation is performed in the presence of a pyrophosphatase and various glycosyltransferases, such as sialyltransferase (STs), glucosyltransferease, galactosyltransferase, mannosyltransferase, fucosyltransferase, acetylgucosaminyltransferase, and acetylgalactosaminyltransferase. In embodiments, the enzymatic elongation is performed in the presence of CSAS, PmST1, α1,3-GalT or β1,3-GalNAcT. In embodiments, the enzymatic elongation conditions include the presence of a glycosyltransferase. In embodiments, the enzymatic elongation conditions include a glycosyltransferase selected from the group consisting of PmST1, GlcT, GlcNAcT GalNAcT, or GalT.

In embodiments wherein at least one $R^c$ and $R^d$ comprises a disaccharide, the method further comprises repeating the enzymatic elongation reaction to form the disaccharide. The enzymatic elongation reaction can be repeated consecutively to extend $R^c$ and/or $R^d$ to be a disaccharide, trisaccharide, tetrasaccharide, or a combination thereof.

In some embodiments, the method can further includes a step of preparing compound (1) by a method including admixing a compound (2A) with sodium methoxide in solution (2A)

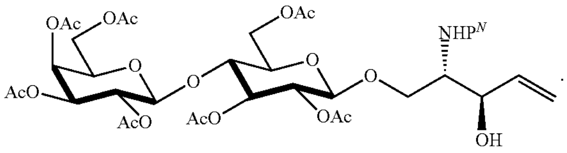

In embodiments, the solution includes methanol and dichloromethane. In embodiments, the admixing of compound (2A) with sodium methoxide can be at room temperature for a time sufficient to complete conversion of the acetate groups to hydroxyl groups, for example, from about 1 hour to about 5 hours, about 2 hours to about 4 hours, or about 3 hours. As reaction times increase above about 3 hours, the protecting group, $P^N$, can be undesirably removed in the presence of sodium methoxide.

In some embodiments, the method further includes preparing compound (2A) by coupling a compound (3) to a protected disaccharide of compound (4), which can be followed by conversion to compound (1), as shown in the following scheme:

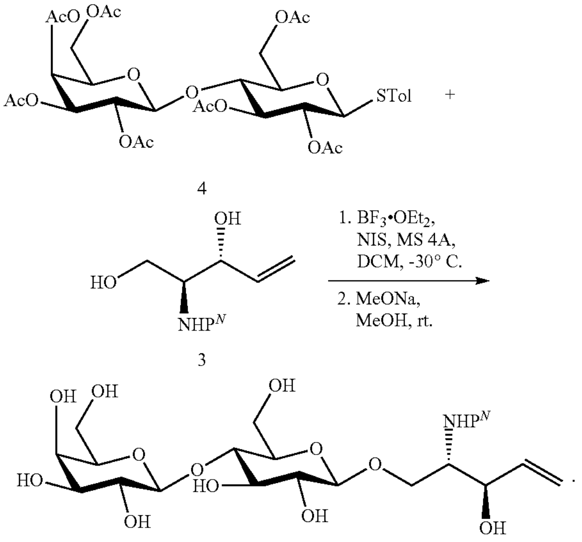

4

3

1

In embodiments, the compound (3) is coupled to the compound (4) at a temperature of at least about −40° C., at least about −35° C., at least about −30° C., and at most about −10° C., at most about −15° C., and at most about −20° C. The compound (3) and the compound (4) can be reacted in a solvent including a polar solvent including, but not limited to, dichloromethane, ethanol, methanol, or a combination thereof. In embodiments, compound (3) and the compound (4) can be provided in a molar ratio of about 3:1 to about 1:3, or about 2:1 to about 1:2, about 1.5:1 to about 1:1.5, about 1.25:1 to about 1:1.25, or about 1:1. In embodiments, the compound (3) and the compound (4) can be provided in a molar ratio of about 1.25:1 to about 1:1.25, or about 1:1. Without intending to be bound by theory, it is believed that when the compound (3) and the compound (4) are provided in a molar ratio of about 1.25:1 to about 1:1.25, there is no byproduct formed from reaction with secondary alcohol on the acceptor observed.

The disclosure further provides a glycan intermediate of Formula (II):

(II)

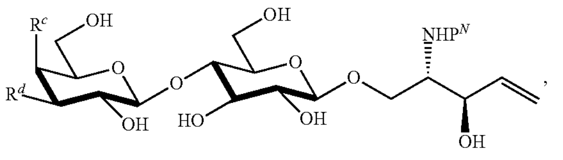

wherein each of $R^c$ and $R^d$ independently comprise OH or a monosaccharide, disaccharide, trisaccharide, or a tetrasaccharide and $P^N$ is Boc, Fmoc, Cbz, or Troc, $HP^N$ together form Phth, or $NHP^N$ together form $N_3$.

In embodiments, $R^c$ is OH. In embodiments, $R^c$ is a monosaccharide, disaccharide, trisaccharide, or a tetrasaccharide. In embodiments, $R^c$ is a monosaccharide or disaccharide. In embodiments, $R^d$ is OH. In embodiments, $R^d$ comprises sialic acid. In embodiments, $R^c$ is OH and $R^d$ is sialic acid. In embodiments, $R^d$ is OH and $R^c$ comprises is galactose. In embodiments, the monosaccharide, disaccharide, trisaccharide, or tetrasaccharide comprises sialic acid, galactose, galactosamine, an unnatural sugar, of a combination thereof. In embodiments, the monosaccharide, disaccharide, trisaccharide, or tetrasaccharide comprises sialic acid, galactose, galactosamine, or a combination thereof.

In embodiments, $P^N$ is Boc. In embodiments, $P^N$ is Fmoc. In embodiments, $P^N$ is Cbz. In embodiments, $P^N$ is Troc.

In embodiments, the glycan intermediate of Formula (II) can have a structure selected from the group consisting of:

(2)

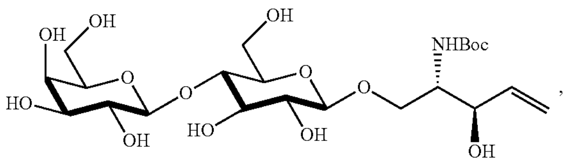

(2.1)

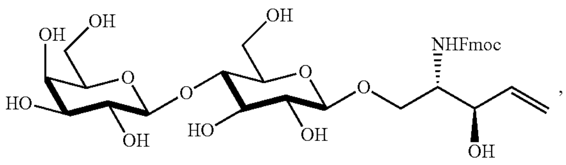

(2.2)

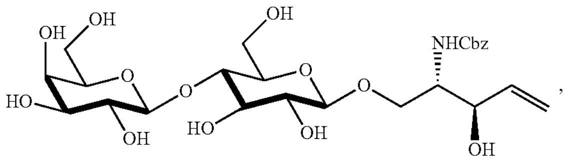

(2.3)

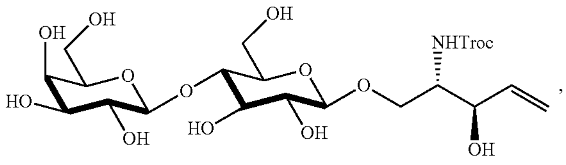

-continued
(5)
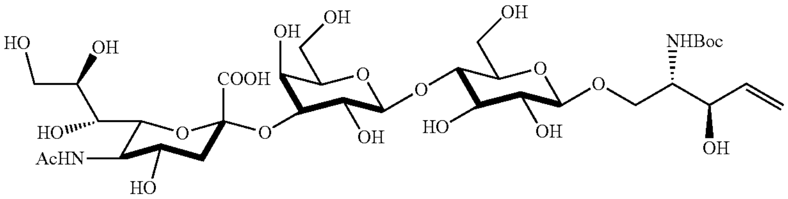
,
(5.1)
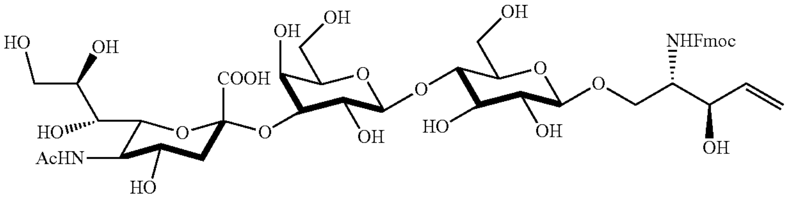
,
(5.2)
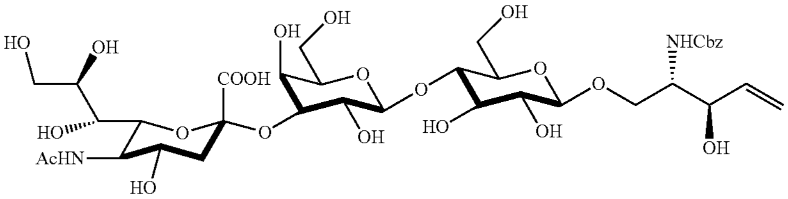
,
(5.3)
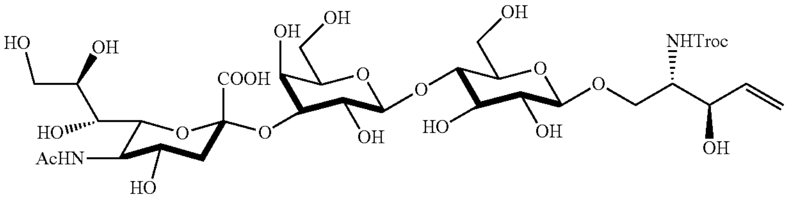
,
(6)
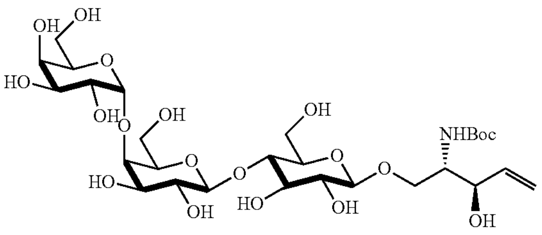
,
(6.1)
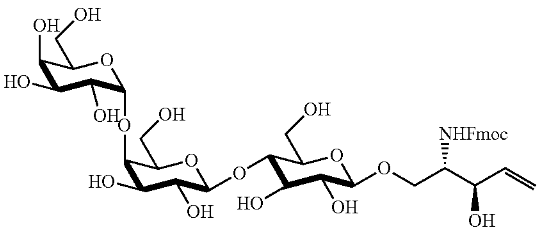
,
(6.2)
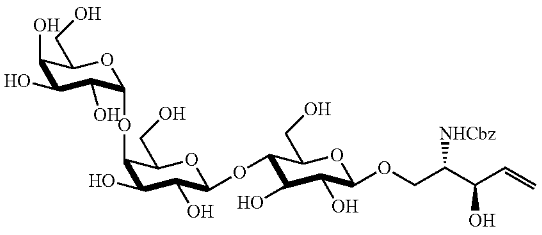
,
(6.3)
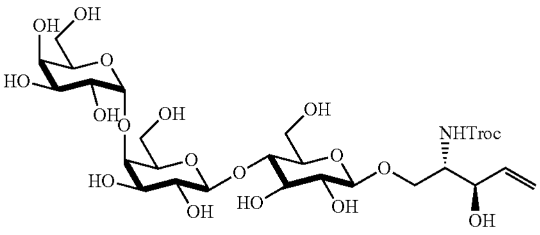
,
(7)
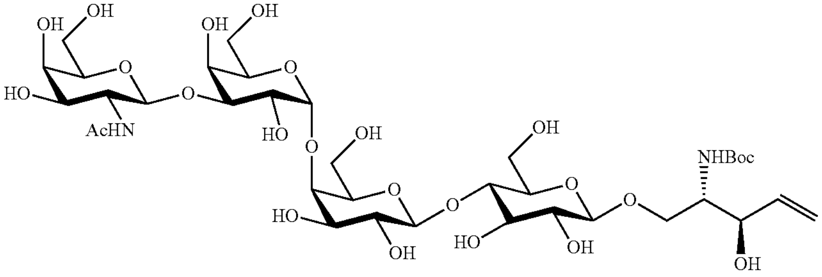
, -continued (7.1)

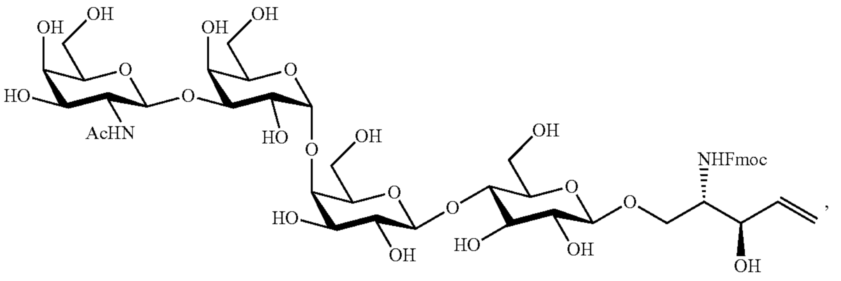

(7.2)

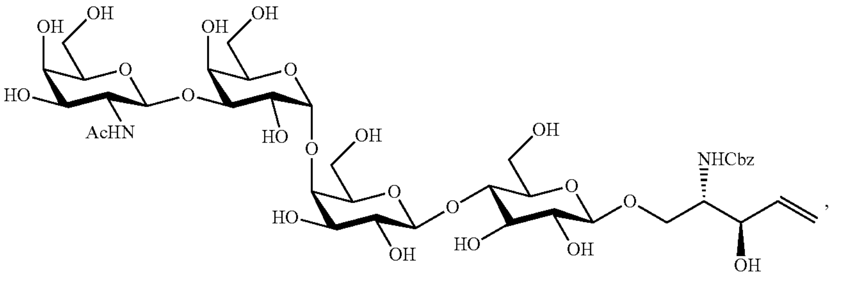

and (7.3)

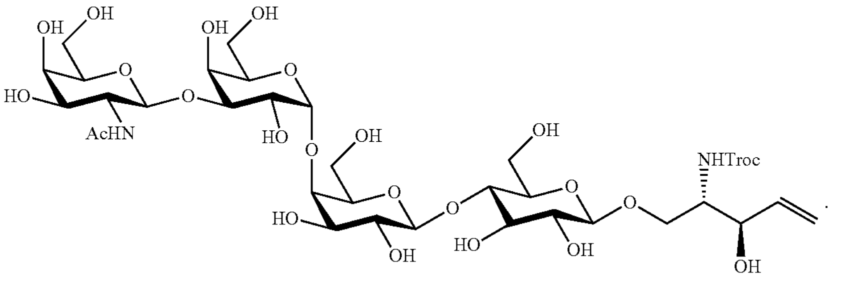

The disclosure further provides an alkene intermediate of Formula (IV):

(IV)

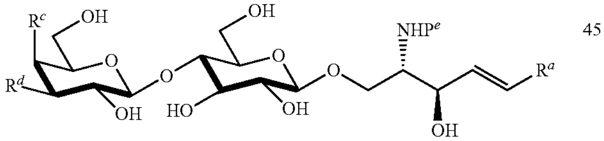

wherein $R^a$ is a $C_{1-30}$alkyl; each of $R^c$ and $R^d$ independently comprise OH or a monosaccharide, disaccharide, trisaccharide, or tetrasaccharide; and $R^e$ is H, Boc, Fmoc, Cbz, or Troc.

In embodiments, $R^c$ is OH. In embodiments, $R^c$ is a monosaccharide, disaccharide, trisaccharide, or tetrasaccharide. In embodiments, $R^c$ is a monosaccharide or disaccharide. In embodiments, $R^d$ is OH. In embodiments, $R^d$ is a monosaccharide, disaccharide, trisaccharide, or tetrasaccharide. In embodiments, $R^d$ is a monosaccharide or disaccharide. In embodiments, $R^d$ comprises sialic acid. In embodiments, the monosaccharide, disaccharide, trisaccharide, or tetrasaccharide comprises an unnatural sugar. In embodiments, the monosaccharide, disaccharide, trisaccharide, or tetrasaccharide comprises sialic acid, galactose, of galactosamine. In embodiments, $R^c$ is OH and $R^d$ comprises sialic acid. In embodiments, $R^d$ is OH and $R^c$ comprises galactose.

In embodiments, $R^e$ is H, Boc, Fmoc, Cbz, or Troc, $HR^e$ together form Phth, or $NHR^e$ together form $N_3$. In embodiments, $R^e$ is H. In embodiments, $R^e$ is Boc. In embodiments, $R^e$ is Fmoc. In embodiments, $R^e$ is Cbz. In embodiments, $R^a$ is a $C_{1-30}$alkyl. In embodiments, $R^a$ is a $C_{2-20}$alkyl. In embodiments, $R^a$ is a $C_{2-18}$alkyl. In embodiments, $R^a$ is a $C_{10-20}$alkyl. In embodiments, $R^a$ is a $C_{13}$alkyl. In embodiments, $R^a$ is a $C_{11}$alkyl.

In embodiments, the alkene intermediate can have a structure selected from the group consisting of:

(8)

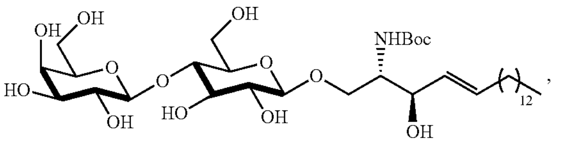

(8.1)

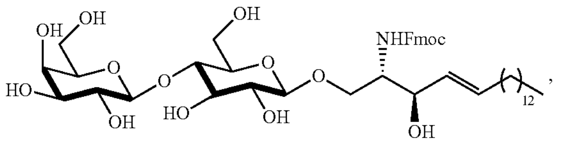

-continued
(8.2)
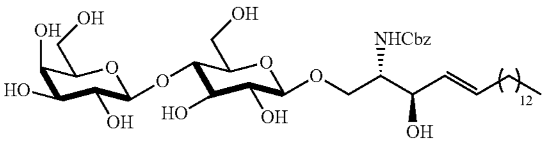,
(8.3)
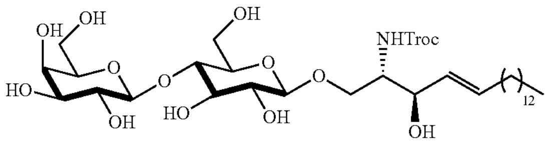
(9)
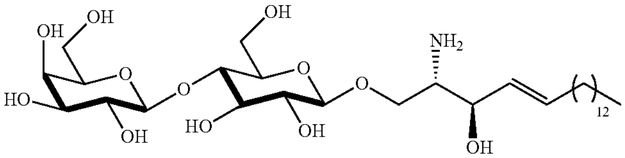,
(10)
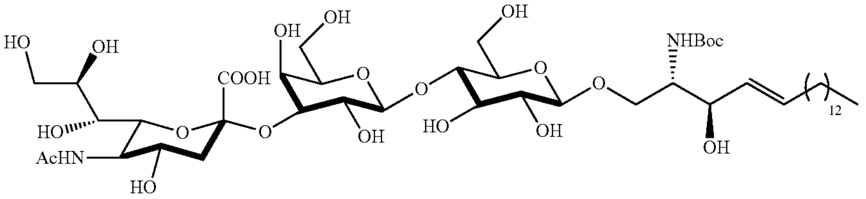,
(10.1)
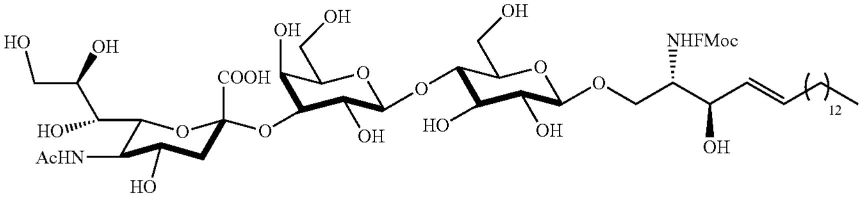,
(10.2)
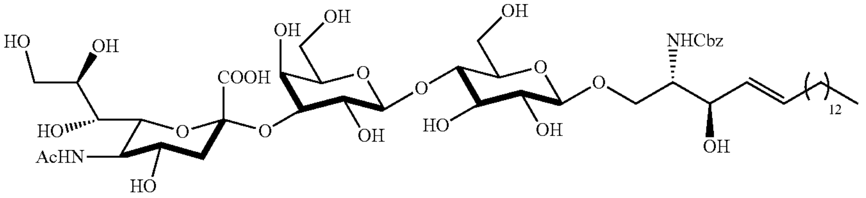,
(10.3)
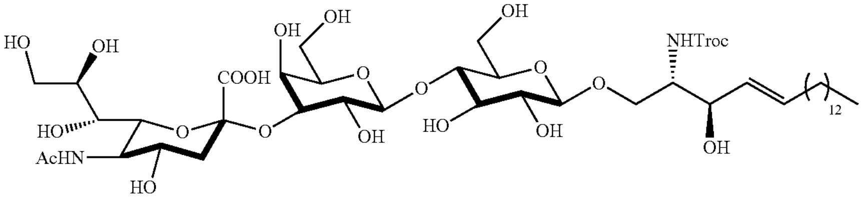,
(11)
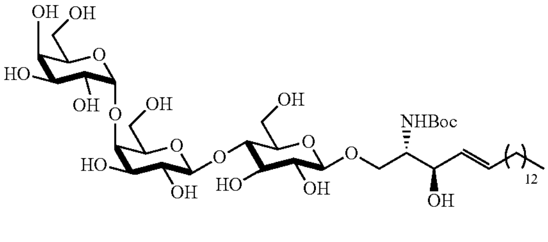,
(11.1)
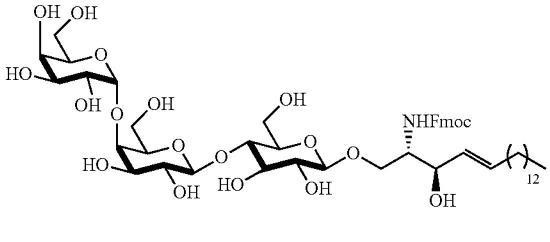, -continued
(11.2)
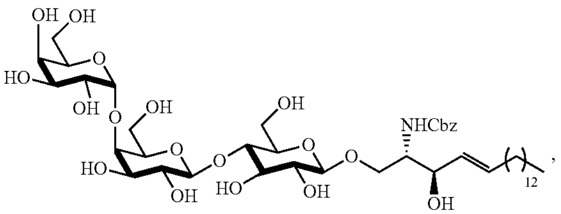
(11.3)
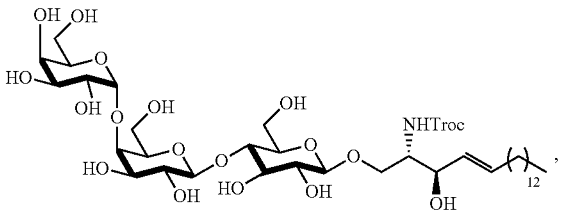
(12)
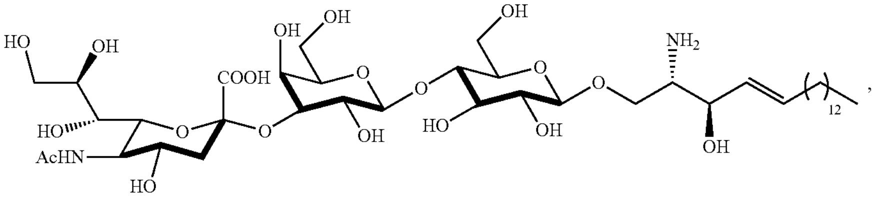
(13)
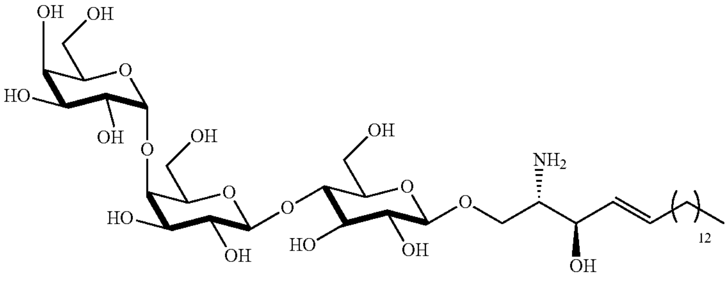
(14)
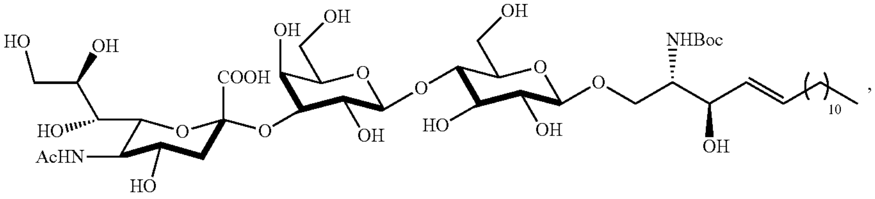
(14.1)
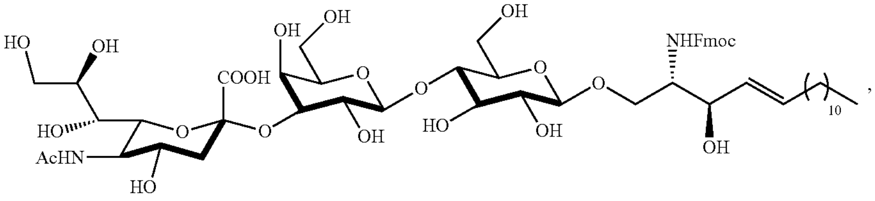
(14.2)
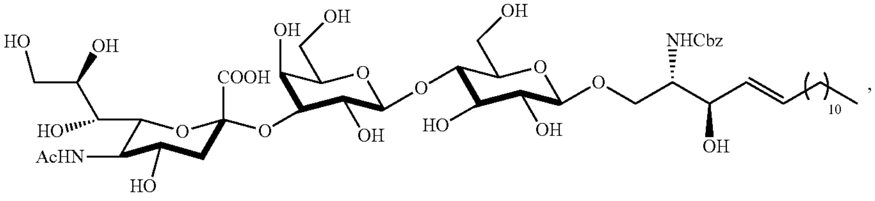
(14.3)
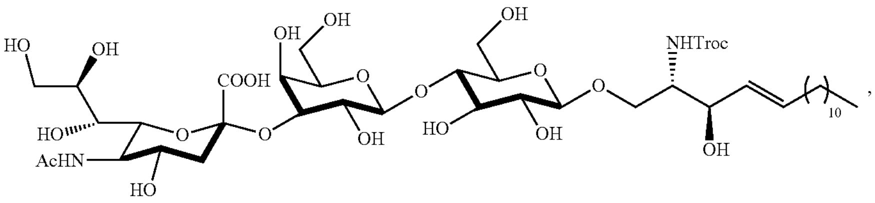

-continued (15)

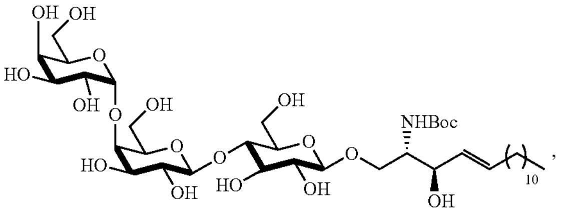

(15.1)

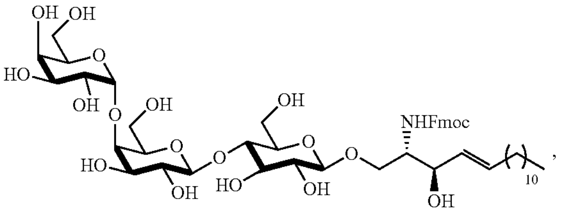

(15.2)

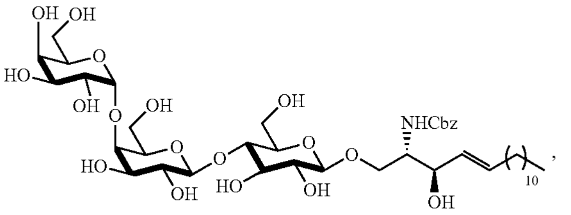

(15.3)

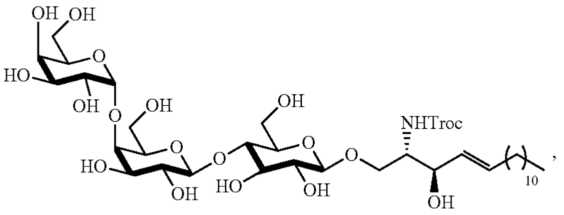

(16)

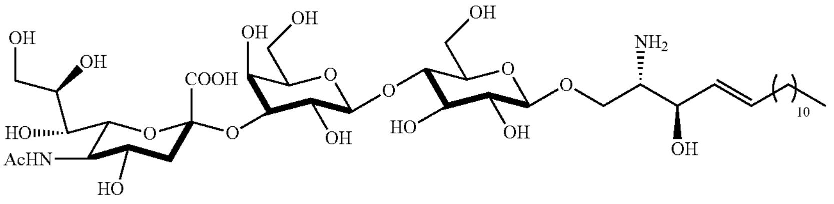

and (17)

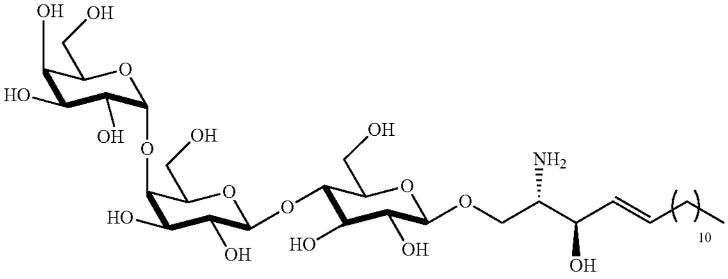

EXAMPLES

Chemicals and materials were purchased from commercial sources and were used as received without further purification unless otherwise noted. Molecular sieves 4 Å were flame-dried under high vacuum and used immediately after cooling to room temperature under a $N_2$ atmosphere. Analytical TLC was carried out on silica gel 60 Å $F_{254}$ plates with detection by a UV detector and/or by charring with 10% (v/v) $H_2SO_4$ in ethanol. Flash column chromatography was performed on silica gel 60 (230-400Mesh). NMR spectra were acquired on a Bruker® or Agilent® 600 MHz spectrometer with chemical shifts reported in ppm (δ) referenced to $CD_3OD$ ($^1H$ NMR δ 3.31 ppm, $^{13}C$ NMR δ 77.0 ppm). Peak and coupling constant assignments are based on $^1H$ NMR, $^1H$-$^1H$ COSY, and $^1H$-$^{13}C$ HMQC experiments.

Example 1

(2S,3R)-5-[β-galactopyranosyl-(1→4)-β-glucopyranosyl-(1→1)]-2-N-tert-Butyloxycarbonylamino-4-pentene-1,3-diol (1)

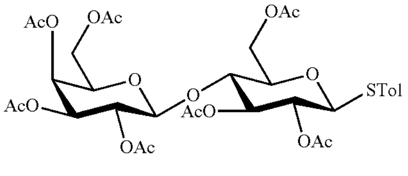

+

4

-continued

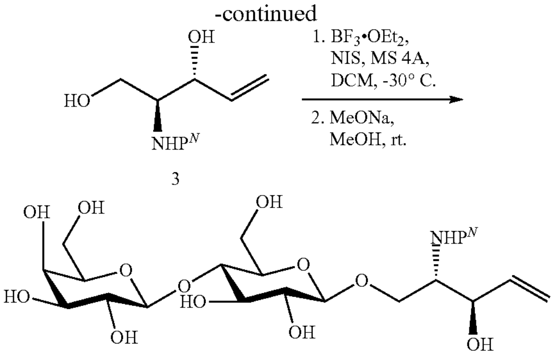

3

1

Lactosyl thioglysoside 4 (742 mg, 1.0 mmol) and diol acceptor 3 (217 mg, 1.0 mmol) were dissolved in 50 mL of anhydrous DCM in presence of 5 g molecular sieves. The mixture was stirred at room temperature for 0.5 h under Argon before cooling to −78° C. N-Iodosuccinimide (NIS) (250 mg, 1.1 mmol) and $BF_3$·$OEt_2$ (36 μL, 0.3 mmol) were added and the reaction mixture was allowed to warm up slowly to −20° C. where activation of the donor 4 was observed by color change. The reaction was kept at −20° C. and monitored by TLC. Upon completion, the reaction was quenched by addition of trimethylamine and filtered through a pad of celite. The filtrate was concentrated under vacuum and the residue was dissolved in DCM/MeOH (60 mL, 1:1, v/v). A MeONa/MeOH solution (0.4 M) was added at 0° C. until the pH reached 10. The solution was stirred at room temperature (~23° C.) for 3 h. When the TLC showed the completion of the reaction, the reaction was neutralized to pH 6-7 with Amberlyst (H+) resin. The resin was removed by filtration and the filtrate was concentrated in vacuum to give the crude product, which was purified by flash column chromatography (MeOH/DCM/$H_2O$, 1:4:0.1, v/v) to give 1 (389 mg, 72%) as a white solid.

$^1$H NMR (600 MHz, MeOD) δ 5.90 (m, 1H), 5.28 (d, 1H, J=17.2 Hz), 5.15 (d, 1H, J=10.4 Hz), 4.36 (d, 1H, J=7.6 Hz), 4.30 (d, 1H, J=7.6 Hz), 4.13-4.11 (m, 2H), 3.91-3.76 (m, 5H), 3.72-3.64 (m, 2H), 3.61-3.52 (m, 5H), 3.49 (dd, 1H, J=9.8, 3.3 Hz), 3.43-3.41 (m, 1H), 3.35 (s, 1H), 3.27 (t, 1H, J=8.1 Hz), 1.43 (s, 9H).

$^{13}$C NMR (151 MHz, MeOD) δ 158.30, 139.61, 116.82, 105.11, 104.49, 80.51, 80.25, 77.08, 76.45, 76.15, 74.81, 74.76, 73.48, 72.54, 70.30, 70.08, 62.49, 61.75, 56.08, 28.78.

Thus, example 1 shows the preparation of compound (1) of the disclosure according to the methods of the disclosure.

Example 2

(2S,3R,4E)-5-[β-galactopyranosyl-(1→4)-β-glucopyranosyl-(1→1)]-2-N-tert-Butyloxycarbonylamino-4-octadecene-1,3-diol (8)

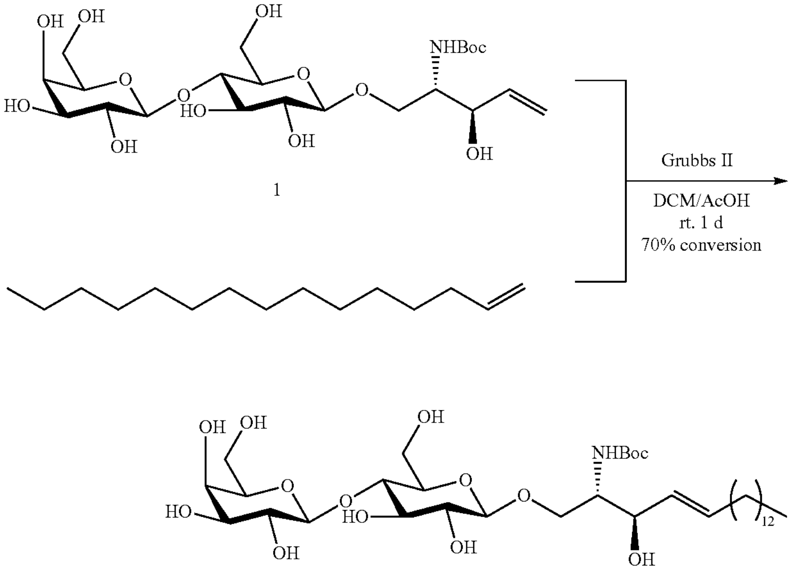

1

8

To a solution of pentadecene (420 mg, 2 mmol) and 1 (108 mg, 0.2 mmol) in DCM/AcOH (5 mL, 1:1, v/v) was added Grubbs-Hoveyda II catalyst (37 mg, 0.06 mmol). The reaction mixture was stirred at room temperature overnight. TLC indicated no progress after about 70% consumption of compound 1. The solvent was removed under vacuum and the residue was purified by flash column chromatography (MeOH/DCM, 1:10, v/v) to give 8 (73 mg, 50%) as a white solid.

$^1$H NMR (600 MHz, MeOD) δ 5.70 (dt, 1H, J=15.3, 6.6 Hz), 5.48 (dd, 1H, J=15.3, 7.7 Hz), 4.36 (d, 1H, J=7.6 Hz), 4.29 (d, 1H, J=7.9 Hz), 4.12 (dd, 1H, J=9.9, 4.7 Hz), 4.05 (t, 1H, J=7.8 Hz), 3.91-3.76 (m, 5H), 3.70 (dd, 1H, J=11.5, 4.6 Hz), 3.63-3.52 (m, 6H), 3.48 (dd, 1H, J=9.8, 3.3 Hz), 3.43-3.40 (m, 1H), 3.35 (s, 1H), 3.27 (t, 1H, J=8.1 Hz), 2.03 (t, 2H, J=7.1 Hz), 1.43 (s, 9H), 1.30 (m, 18H), 0.90 (t, 3H, J=6.9 Hz).

$^{13}$C NMR (151 MHz, MeOD) δ 158.33, 105.09, 104.43, 80.49, 80.22, 77.07, 76.41, 76.13, 74.79, 74.75, 73.31, 72.52, 70.49, 70.28, 62.48, 61.71, 56.17, 56.08, 49.85, 47.90, 28.79, 27.55, 10.45, 9.23.

Thus, Example 2 shows how to prepare an alkene intermediate of the disclosure using methods of the disclosure.

Example 3

(2S,3R,4E)-5-[β-galactopyranosyl-(1→4)-β-glucopyranosyl-(1→1)]-2-amino-4-octadecene-1,3-diol (9)

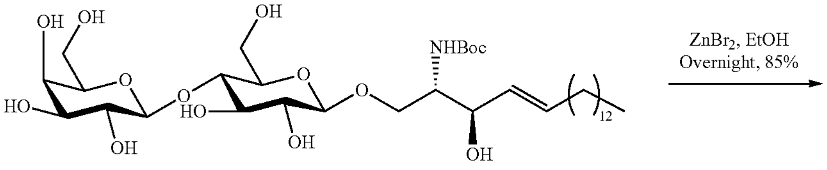

8

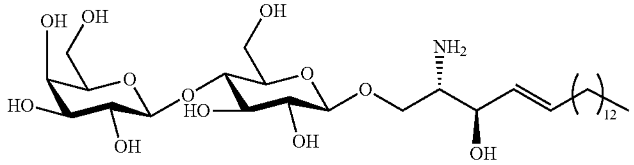

9

To a solution of 8 (73 mg, 0.1 mmol) in methanol (2 mL) was added zinc bromide (450 mg, 2 mmol). The resulting mixture was stirred overnight at room temperature until TLC indicated completion of the reaction. The solvent was reduced under vacuum and the residue was passed through a short silica gel column chromatography (MeOH/DCM, 1:3, v/v, with 1% concentrated $NH_4OH$ solution in water) to remove zinc bromide. The crude product was subject to the following reaction without further purification.

Thus, Example 3 shows how to prepare an alkene intermediate of the disclosure according to methods of the disclosure.

Example 4

(2S,3R,4E)-5-[β-galactopyranosyl-(1→4)-β-glucopyranosyl-(1→1)]-2-(hexadecanamido)-4-octadecene-1,3-diol (7)

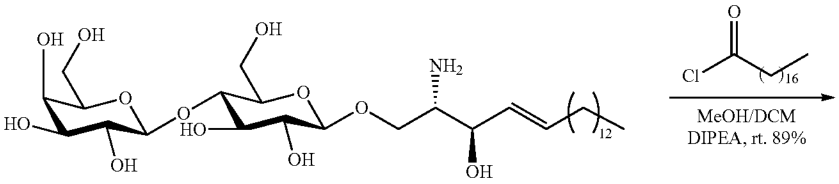

9

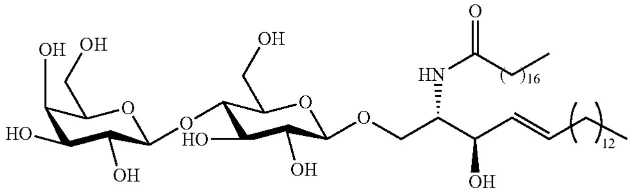

18

To the solution of 9 (crude product from Example 3, ~0.1 mmol) in DCM/MeOH (5 mL, 1:1, v/v) was added stearoyl chloride (151 mg, 0.5 mmol) followed by DIPEA (129 mg, 1 mmol). The reaction mixture was stirred overnight at room temperature until complete consumption of 9, as indicated by TLC. The solvent was removed under vacuum and the residue was purified by flash column chromatography (MeOH/DCM, 1:10, v/v) to give 18 (69 mg, 78% for 2 steps) as a white solid.

Thus, Example 4 shows how to prepare a GSL of the disclosure according to methods of the disclosure.

Example 5

(2S,3R)-5-[Acetyl-α-neuraminyl-(2→3)-β-galactopyranosyl-(1→4)-β-glucopyranosyl-(1→1)]-2-N-tert-Butyloxycarbonylamino-4-pentene-1,3-diol (5)

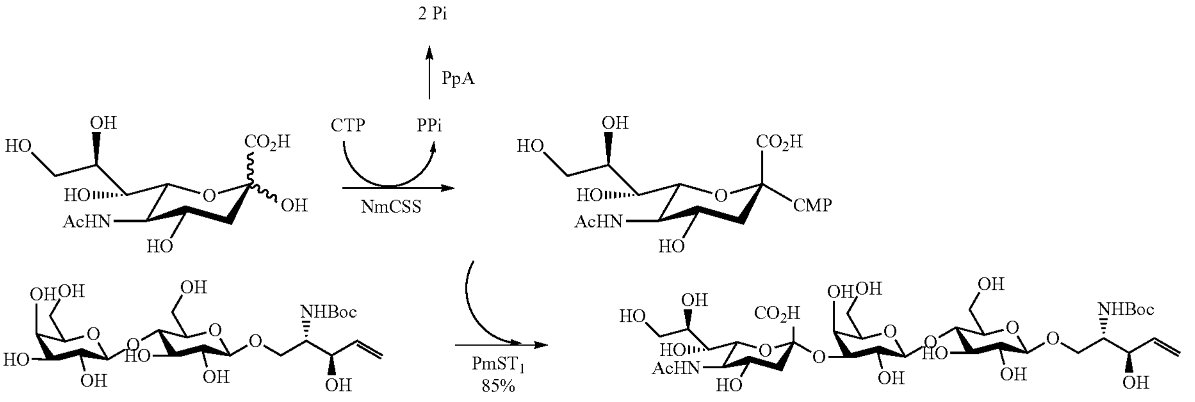

1

5

Lactosyl acceptor 1 (54 mg, 0.1 mmol, 20 mM), N-acetylneuraminic acid (Neu5Ac) (46 mg, 0.15 mmol, 30 mM), and cytidine triphosphate (CTP) (73 mg, 0.15 mmol, 30 mM) were dissolved in 5 mL of Tris-HCl buffer (50 mM pH 8.0) with 15 mM of $MgCl_2$. 0.1 mg of CMP-sialic acid synthetase (NmCSS), 0.1 mg of PmST1, and 0.02 mg of PmPpA were added prior to readjusting the pH to 8.0. The reaction was incubated at 37° C. with agitation at 120 rpm. The reaction was monitored by TLC ($EtOAc/MeOH/H_2O/HOAc$=5:2:1.4:0.4) and the lactose was consumed in about 2 hours. The reaction was quenched by adding an equal volume of cold ethanol and kept at −80° C. for 1 h. The mixture was centrifuged at 13,000 rpm for 30 minutes. The supernatant was concentrated and purified by flash column chromatography on silica gel. Product 5 was obtained as a white solid (70 mg, 85%).

Thus, Example 5 shows preparation of a glycan intermediate of the disclosure using methods according to the disclosure.

Example 6

(2S,3R)-5-[α-galactopyranosyl-(1→4)-β-galactopyranosyl-(1→4)-β-glucopyranosyl-(1→1)]-2-N-tert-Butyloxycarbonylamino-4-pentene-1,3-diol (6)

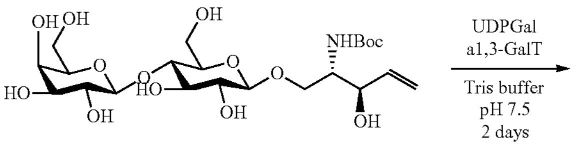

2.0 equiv
1

-continued

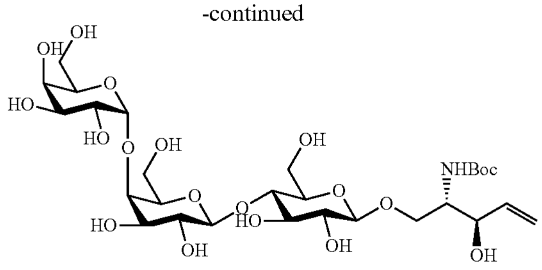

80%
6

Lactosyl acceptor 1 (54 mg, 0.1 mmol, 20 mM) and UDP-Gal (28 mg, 0.05 mmol, 10 mM), were dissolved in 5 mL of Tris-HCl buffer (100 mM pH 7.5) with 5 mM dithiothreitol and 1 mM $MnCl_2$. The reaction was initiated by addition of α1,3-GalT (LgtC, 2.5 U) and incubated at room temperature for 2 days with agitation at 120 rpm. Then it was quenched by adding an equal volume of cold ethanol and kept at −80° C. for 1 h. The mixture was centrifuged at 13,000 rpm for 30 minutes. The supernatant was concentrated and purified by flash column chromatography on silica gel. Product 6 was obtained as a white solid (28 mg, 80%).

$^1$H NMR (600 MHz, $D_2O$) δ 7.89 (d, 1H, J=8.2 Hz), 5.90 (m, 1H), 5.22 (m, 1H), 4.86 (d, 1H, J=1.8 Hz), 4.40 (m, 2H), 4.32-4.26 (m, 3H), 4.20 (s, 1H), 4.14-4.09 (m, 2H), 3.95-3.90 (m, 4H), 3.86-3.81 (m, 3H), 3.77-3.48 (m, 15H), 3.25 (m, 1H), 3.11 (q, 2H, J=7.3 Hz), 1.35-1.33 (br, 9H), 1.19 (t, 3H, J=7.3 Hz).

$^{13}$C NMR (151 MHz, $D_2O$) δ 157.97, 136.24, 117.96, 103.26, 102.27, 100.30, 81.19, 78.65, 77.35, 75.41, 74.76, 74.26, 72.88, 72.14, 70.89, 70.81, 69.11, 68.93, 68.55, 60.50, 60.36, 60.00, 54.27, 46.66, 27.67, 27.64, 25.49, 9.21, 8.22. HRMS $[M+Na]^+$ m/z calcd for $C_{28}H_{49}NNaO_{19}^+$ 726.2791, found 726.2759.

Thus, Example 6 shows preparation of a glycan intermediate of the disclosure using methods according to the disclosure.

Example 7

(2S,3R)-5-[β-(2-deoxy-2-N-Acetyl-galactopyranosyl)-(1→3)-α-galactopyranosyl-(1→4)β-galactopyranosyl-(1→4)-β-glucopyranosyl-(1→1)]-2-N-tert-Butyloxycarbonylamino-4-pentene-1,3-diol (7)

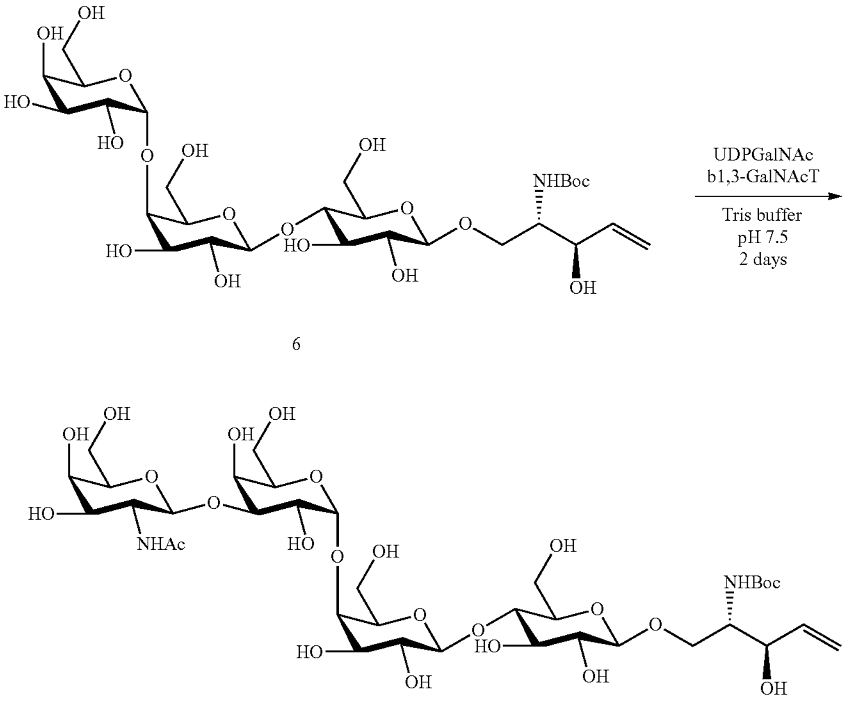

6

70%
7

Gb3 acceptor 6 (28 mg, 0.04 mmol, 20 mM) and UDP-GalNAc (28 mg, 0.044 mmol, 22 mM), were dissolved in 2 mL of Tris-HCl buffer (100 mM pH 7.5) with 5 mM dithiothreitol and 1 mM $MnCl_2$. The reaction was initiated by addition of β1,3-GalNAcT (LgtD, 1 U). The reaction mixture was incubated at room temperature for 2 days with agitation at 120 rpm. Then it was quenched by adding an equal volume of cold ethanol and kept at −80° C. for 1 h. The mixture was centrifuged at 13,000 rpm for 30 minutes. The supernatant was concentrated and purified by flash column chromatography on silica gel. Product 7 was obtained as a white solid (25 mg, 70%).

$^1$H NMR (600 MHz, $D_2O$) δ 5.79 (m, 1H), 5.26 (dt, 1H, J=7.2, 1.3 Hz) 5.20 (d, 1H, J=10.6 Hz), 4.84 (d, 1H, J=3.9 Hz), 4.55 (d, 1H, J=8.4 Hz), 4.43 (d, 1H, J=7.7 Hz), 4.40 (d, 1H, J=8.0 Hz), 4.30 (t, 1H, J=6.2 Hz), 4.17 (d, 1H, J=2.5 Hz), 4.11 (t, 1H, J=6.7 Hz), 3.95 (d, 1H, J=3.1 Hz), 3.93-3.81 (m, 7H), 3.78-3.64 (m, 8H), 3.63-3.54 (m, 6H), 3.52-3.48 (m, 4H), 3.26 (m, 1H), 1.36-1.34 (br, 9H), 1.10 (t, 3H, J=7.1 Hz). $^{13}$C NMR (151 MHz, $D_2O$) δ 175.15, 157.97, 136.22, 117.96, 103.29, 103.23, 102.25, 100.40, 81.19, 78.74, 78.70, 77.21, 75.42, 74.92, 74.76, 74.29, 72.90, 72.10, 70.87, 70.78, 70.26, 69.14, 68.93, 67.75, 67.60, 62.10, 60.98, 60.36, 60.30, 60.01, 57.40, 54.25, 52.58, 27.65, 27.63, 25.49, 22.24, 16.76, 9.20.

Thus, example 7 shows preparation of a glycan intermediate of the disclosure using methods according to the disclosure.

Example 8

(2S,3R,4E)-5-[Acetyl-α-neuraminyl-(2→3)-β-galactopyranosyl-(1→4)-β-glucopyranosyl-(1→1)]-2-hexadecanamido-4-octadecene-1,3-diol (19, GM3)

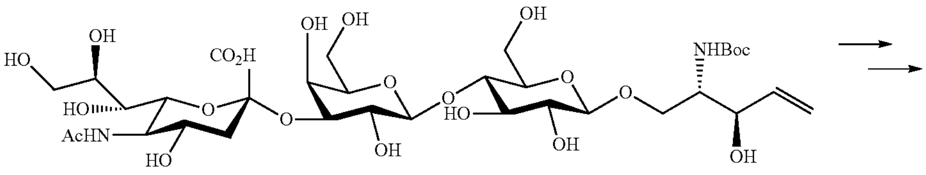

5

-continued

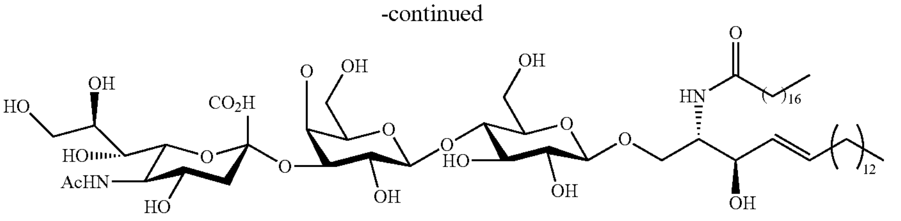

19

The synthesis of compound 19 from compound 5 was similar to the procedure for the synthesis of compound 18 from compound 1 with only minor adjustment of solvent ratio in the Grubbs catalyst-mediated olefin metathesis reaction from DCM/AcOH 1:1 to 1:2 in order to dissolve the substrates.

$^1$H NMR (600 MHz, MeOD) δ 5.68 (dt, 1H, J=15.2, 6.8 Hz), 5.44 (dd, 1H, J=15.2, 7.9 Hz), 4.43 (d, 1H, J=7.9 Hz), 4.30 (d, 1H, J=7.9 Hz), 4.19 (dd, 1H, J=10.1, 4.4 Hz), 4.09-4.04 (m, 2H), 3.98-3.83 (m, 6H), 3.79-3.53 (m, 11H), 3.48 (dd, 1H, J=9.0, 1.8 Hz), 3.43-3.41 (m, 2H), 3.35 (d, 1H, J=2.2 Hz), 3.19 (m, 1H), 2.87-2.85 (m, 1H), 2.17 (t, 2H, J=7.5 Hz), 2.01 (m, 5H), 1.73 (t, 1H, 11.6 Hz), 1.59-1.56 (m, 2H), 1.28 (m, 50H), 0.90 (t, 6H, J=6.8 Hz).

$^{13}$C NMR (151 MHz, MeOD) δ 175.95, 175.48, 174.92, 135.00, 131.40, 105.11, 104.50, 101.10, 80.89, 77.70, 77.09, 76.47, 76.25, 74.95, 74.83, 72.96, 70.86, 70.12, 69.87, 69.41, 68.99, 66.13, 64.66, 62.74, 54.74, 53.95, 49.57, 42.11, 37.38, 33.47, 33.11, 33.09, 30.88, 30.85, 30.83, 30.81, 30.77, 30.71, 30.64, 30.52, 30.48, 30.44, 27.18, 23.76, 23.75, 22.56, 17.82, 17.41, 14.45.

HRMS $[M]^+$ m/z calcd for $C_{59}H_{107}N_2O_{21}$ 1179.7372, found 1179.7247.

Thus, Example 8 shows the preparation of a GSL according to the methods of the disclosure.

Example 9

(2S,3R,4E)-5-[α-galactopyranosyl-(1→4)-β-galactopyranosyl-(1→4)-β-glucopyranosyl-(1→1)]-2-hexadecanamido-4-octadecene-1,3-diol (20, Gb3)

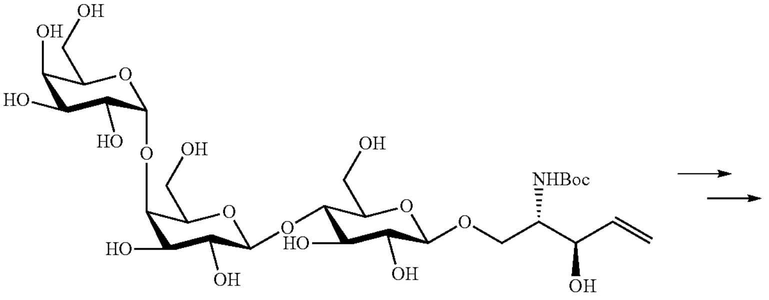

6

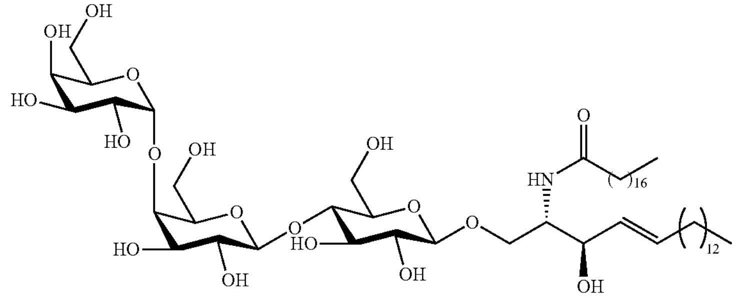

20

The synthesis of compound 20 from compound 6 was similar to the procedure for the synthesis of compound 18 from compound 1 with only minor adjustment of solvent ratio in the Grubbs catalyst-mediated olefin metathesis reaction from DCM/AcOH 1:1 to 1:2 in order to dissolve the substrates.

$^1$H NMR (600 MHz, MeOD) δ 7.87 (d, 1H, J=9.3 Hz), 5.69 (dt, 1H, J=15.2, 6.8 Hz), 5.44 (dd, 1H, J=15.2, 7.9 Hz), 4.96 (d, 1H, J=3.8 Hz), 4.41 (d, 1H, J=6.8 Hz), 4.31 (d, 1H, J=7.9 Hz), 4.26 (d, 1H, J=6.0 Hz), 4.17 (dd, 1H, J=10.0, 4.6 Hz), 4.06 (t, 1H, J=8.1 Hz), 3.98 (m, 1H), 3.92-3.88 (m, 2H), 3.84-3.81 (m, 2H), 3.78-3.65 (m, 7H), 3.60-3.49 (m, 6H), 3.43-3.35 (m, 3H), 2.17 (t, 2H, J=7.5 Hz), 2.04 (m, 2H), 1.58 (m, 2H), 1.42-1.26 (m, 48H), 0.90 (t, 1H, J=6.8 Hz).

$^{13}C$ NMR (151 MHz, MeOD) δ 175.98, 135.11, 131.35, 105.39, 104.46, 102.69, 80.93, 79.77, 78.24, 76.53, 76.47, 76.25, 74.95, 73.02, 72.84, 72.65, 71.29, 71.06, 70.54, 69.97, 62.69, 61.75, 61.46, 59.92, 49.57, 47.93, 37.39, 33.47, 33.10, 33.08, 30.88, 30.85, 30.82, 30.81, 30.77, 30.71, 30.64, 30.51, 30.48, 30.47, 30.45, 30.43, 27.17, 23.75, 14.45, 9.22, 8.21.

HRMS $[M+Na]^+$ m/z calcd for $C_{54}H_{101}NNaO_{18}^+$ 1074.6911, found 1074.6556.

Thus, Example 9 shows the preparation of a GSL according to the methods of the disclosure.

Example 10

(2S,3R,4E)-5-[β-(2-deoxy-2-N-Acetyl-galactopyranosyl)-(1→3)-α-galactopyranosyl-(1→4)-β-galactopyranosyl-(1→4)-β-glucopyranosyl-(1→1)]-2-hexadecanamido-4-octadecene-1,3-diol (21, Gb4)

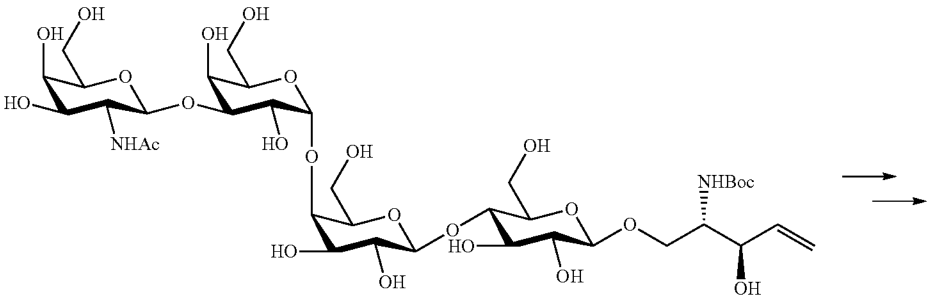

7

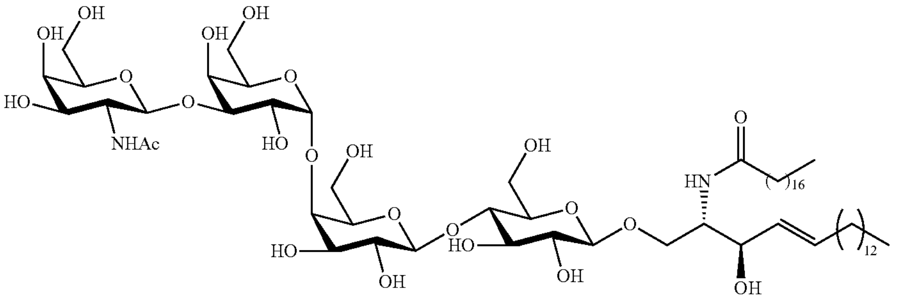

21

The synthesis of compound 21 from compound 7 was similar to the procedure for the synthesis of compound 18 from compound 1 with only minor adjustment of solvent ratio in the Grubbs catalyst-mediated olefin metathesis reaction from DCM/AcOH 1:1 to 1:2 in order to dissolve the substrates.

$^1H$ NMR (600 MHz, MeOD) δ 5.69 (dt, 1H, J=15.3, 6.8 Hz), 5.45 (dd, 1H, J=15.3, 7.9 Hz), 4.95 (d, 1H, J=4.0 Hz), 4.62 (d, 1H, J=8.4 Hz), 4.41 (m, 1H), 4.30 (d, 1H, J=7.9 Hz), 4.27 (t, 1H, J=6.4 Hz), 4.17 (m, 2H), 4.06 (t, 1H, J=8.2 Hz), 3.99-3.93 (m, 4H), 3.90-3.89 (m, 2H), 3.85-3.83 (m, 3H), 3.79-3.67 (m, 5H), 3.62-3.51 (m, 7H), 3.43-3.41 (m, 1H), 3.35-3.27 (m, 7H), 2.17 (t, 2H, J=7.5 Hz), 2.04 (m, 2H), 2.00 (s, 3H), 1.58 (m, 2H), 1.42-1.26 (m, 48H), 0.90 (t, 1H, J=6.8 Hz). $^{13}C$ NMR (151 MHz, MeOD) δ 175.97, 175.03, 135.11, 131.35, 105.49, 104.59, 104.48, 102.76, 81.09, 80.91, 79.98, 76.73, 76.55, 76.45, 76.29, 74.95, 74.67, 73.43, 73.04, 72.54, 72.45, 70.62, 69.99, 69.59, 69.51, 62.60, 61.80, 61.53, 60.17, 54.83, 54.71, 49.57, 37.39, 33.47, 33.11, 33.09, 30.88, 30.85, 30.83, 30.81, 30.77, 30.71, 30.64, 30.51, 30.49, 30.47, 30.46, 30.43, 27.17, 23.76, 23.75, 23.12, 14.46, 14.45, 8.48.

HRMS $[M+Na]^+$ m/z calcd for $C_{62}H_{114}N_2NaO_{23}^+$ 1277.7705, found 1277.7581.

Thus, Example 10 shows the preparation of a GSL according to the methods of the disclosure.

Example 11

(2S,3R,4E)-5-[β-galactopyranosyl-(1→4)-β-glucopyranosyl-(1→1)]-2-N-tert-Butyloxycarbonylamino-4-nonene-1,3-diol (22)

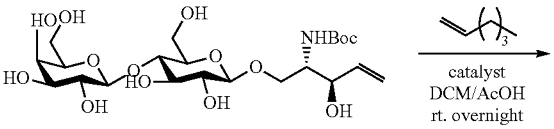

1

-continued

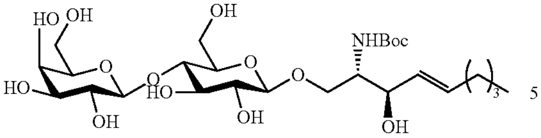

22

Obtained from compound 1 with similar procedure described previously for compound 8.

$^1$H NMR (600 MHz, MeOD) δ 5.69 (dt, 1H, J=15.3, 6.7 Hz), 5.47 (dd, 1H, J=15.3, 7.9 Hz), 4.36 (d, 1H, J=7.6 Hz), 4.29 (d, 1H, J=7.8 Hz), 4.13 (dd, 1H, J=9.9, 4.8 Hz), 4.05 (t, 1H, J=7.8 Hz), 3.91-3.76 (m, 4H), 3.70 (dd, 1H, J=11.5, 4.6 Hz), 3.63-3.52 (m, 6H), 3.48 (dd, 1H, J=9.7, 3.3 Hz), 3.43-3.40 (m, 1H), 3.27 (t, 1H, J=8.1 Hz), 2.05 (m, 2H), 1.43 (s, 9H), 1.39-1.29 (m, 8H), 0.91 (t, 3H, J=7.2 Hz).

$^{13}$C NMR (151 MHz, MeOD) δ 134.81, 131.26, 105.11, 104.52, 80.49, 77.09, 76.45, 76.16, 74.82, 74.77, 73.32, 72.55, 70.30, 62.49, 61.75, 56.19, 33.11, 32.55, 28.82, 23.28, 14.32.

HRMS $[M+Na]^+$ m/z calcd for $C_{26}H_{47}NNaO_{14}^+$ 620.2889, found 620.2880.

Thus, Example 11 shows how to prepare an alkene intermediate of the disclosure using methods of the disclosure.

Example 12

(2S,3R,4E)-5-[β-galactopyranosyl-(1→4)-β-glucopyranosyl-(1→1)]-2-(2-azido-N-acetamido)-4-nonene-1,3-diol (23)

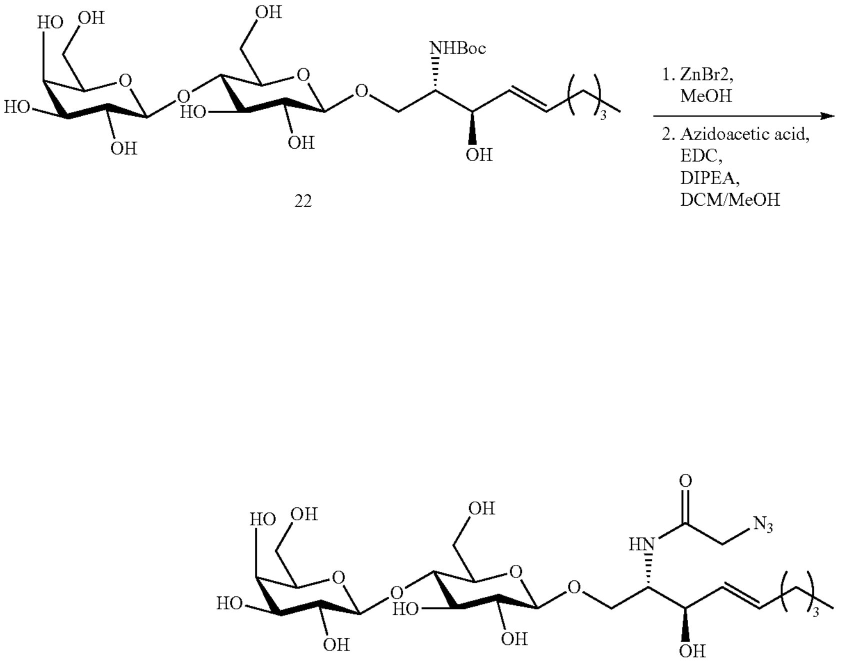

22

23

To a solution of 22 (30 mg, 0.05 mmol) in methanol (1 mL) was added zinc bromide (225 mg, 1 mmol). The resulting mixture was stirred overnight at room temperature until completion of the reaction was indicated by TLC. The solvent was reduced under vacuum and the residue was passed through a short silica gel column (MeOH/DCM, 1:3, v/v, with 1% of concentrated $NH_4OH$ solution in water) to remove zinc bromide. The crude product was subject to following reaction without further purification.

To the solution of this crude product (~0.05 mmol) in DCM/MeOH (5 mL, 1:1, v/v) was added azidoacetic acid (50 mg, 0.5 mmol), EDC·HCl (96 mg, 0.5 mmol), and DIPEA (129 mg, 1 mmol). The reaction mixture was stirred overnight at room temperature until complete consumption of amine as indicated by TLC. The solvent was removed under vacuum and the residue was purified by flash column chromatography (MeOH/DCM, 1:10, v/v) to give 23 (23 mg, 79%) as a white solid.

$^1$H NMR (600 MHz, MeOD) δ 5.69 (dt, 1H, J=15.3, 6.7 Hz), 5.48 (dd, 1H, J=15.3, 7.6 Hz), 4.36 (d, 1H, J=7.8 Hz), 4.29 (d, 1H, J=7.8 Hz), 4.13 (dd, 1H, J=9.9, 4.7 Hz), 4.06 (t, 1H, J=7.8 Hz), 3.91-3.76 (m, 4H), 3.71-3.67 (m, 2H), 3.64-3.52 (m, 6H), 3.48 (dd, 1H, J=9.7, 3.3 Hz), 3.43-3.40 (m, 1H), 3.27 (dd, 1H, J=8.8, 8.1 Hz), 3.19-3.16 (m, 1H), 2.06-2.03 (m, 2H), 1.39-1.29 (m, 6H), 0.91 (t, 3H, J=7.2 Hz).

$^{13}$C NMR (151 MHz, MeOD) δ 158.25, 134.84, 131.25, 105.11, 104.52, 80.49, 80.15, 77.09, 76.45, 76.15, 74.81, 74.77, 73.32, 72.55, 70.30, 70.24, 62.49, 61.74, 56.19, 33.11, 32.54, 28.82, 23.28, 14.32.

HRMS $[M+Na]^+$ m/z calcd for $C_{23}H_{40}N_4NaO_{13}^+$ 603.2484, found 603.2498.

Thus, Example 12 shows preparation of a GSL modified with an azido functional group according to the disclosure prepared using methods of the disclosure.

Example 13

(2S,3R,4E)-5-[β-galactopyranosyl-(1→4)-β-glucopyranosyl-(1→1)]-2-N-(11-N-nitrobenzoxadiazol-4-yl-amino)undecanamide-4-octadecene-1,3-diol (26)

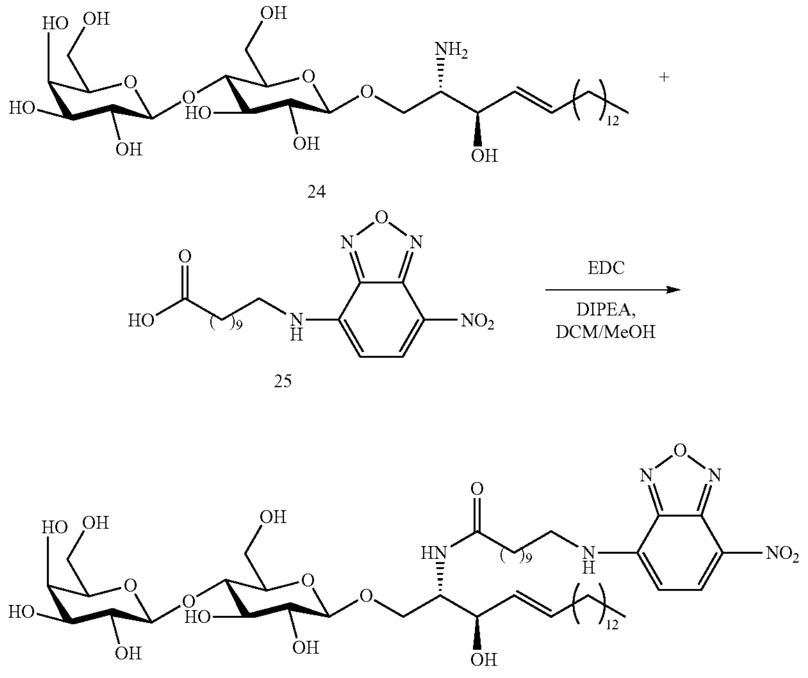

24

25

26

Obtained from compound 24 and 25 with similar procedure described previously for compound 23.

$^1$H NMR (600 MHz, MeOD) δ 8.55 (d, 1H, J=8.9 Hz), 6.37 (d, 1H, J=8.9 Hz), 5.70 (dt, 1H, J=15.3, 6.6 Hz), 5.46 (dd, 1H, J=15.3, 7.7 Hz), 4.37 (d, 1H, J=7.6 Hz), 4.32 (d, 1H, J=7.8 Hz), 4.18 (dd, 1H, J=10.1, 4.7 Hz), 4.09 (d, 1H, J=8.1 Hz), 4.01-3.98 (m, 1H), 3.92 (dd, 1H, J=12.2, 2.6 Hz), 3.86 (dd, 1H, J=12.1, 4.3 Hz), 3.84 (d, 1H, J=3.2 Hz), 3.80 (dd, 1H, J=11.5, 7.5 Hz), 3.72 (dd, 1H, J=11.5, 4.6 Hz), 3.62-3.54 (m, 6H), 3.50 (dd, 1H, J=9.7, 3.3 Hz), 3.45-3.42 (m, 1H), 2.19 (t, 2H, J=7.4 Hz), 2.04 (m, 2H), 1.80 (m, 2H), 1.59 (m, 2H), 1.49 (m, 2H), 1.43-1.27 (m, 34H), 0.90 (t, 1H, J=7.2 Hz).

$^{13}$C NMR (151 MHz, MeOD) δ 175.98, 146.76, 145.90, 138.67, 135.07, 131.32, 119.21, 117.29, 105.14, 104.51, 99.58, 80.60, 77.11, 76.49, 76.28, 74.86, 74.83, 73.02, 72.55, 70.29, 69.95, 62.51, 61.78, 54.74, 44.80, 37.34, 33.44, 33.07, 30.84, 30.81, 30.77, 30.73, 30.65, 30.56, 30.54, 30.48, 30.44, 30.40, 30.38, 29.33, 28.10, 27.11, 23.73, 14.44.

Thus, Example 13 demonstrates preparation of a GSL modified with a fluorescent tag according to the disclosure using methods of the disclosure.

Example 14

(2S,3R,4E)-5-[α-galactopyranosyl-(1→4)-β-galactopyranosyl-(1→4)-β-glucopyranosyl-(1→1)]-2-N-(11-N-nitrobenzoxadiazol-4-yl-amino) undecanamide-4-octadecene-1,3-diol (28)

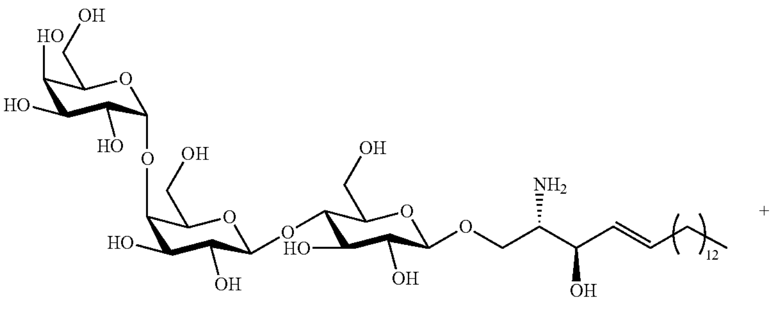

27

-continued

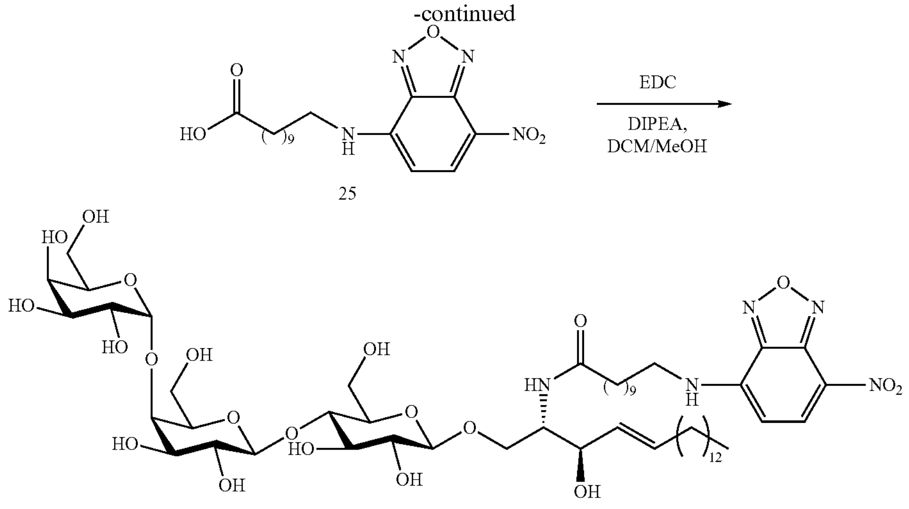

25

28

Obtained from compound 27 and 25 with similar procedure described previously for compound 23.

$^{1}H$ NMR (600 MHz, MeOD) δ 8.53 (d, 1H, J=7.2 Hz), 7.85 (d, 1H, J=9.6 Hz), 6.35 (d, 1H, J=7.2 Hz), 5.68 (dt, 1H, J=15.7, 7.2 Hz), 5.46 (dd, 1H, J=15.7, 7.5 Hz), 4.41 (d, 1H, J=7.2 Hz), 4.30 (d, 1H, J=10.8 Hz), 4.26 (t, 1H, J=6.6 Hz), 4.15 (dd, 1H, J=10.0, 5.3 Hz), 4.07 (t, 1H, J=7.9 Hz), 3.98 (s, 1H), 3.92-3.88 (m, 2H), 3.84-3.81 (m, 2H), 3.78-3.67 (m, 4H), 3.60-3.51 (m, 4H), 3.42-3.40 (m, 2H), 2.17 (t, 2H, J=7.6 Hz), 2.05-1.99 (m, 2H), 1.78 (t, 2H, J=7.9 Hz), 1.60-1.56 (m, 2H), 1.48-1.45 (m, 2H), 1.40-1.25 (m, 24H), 0.88 (t, 1H, J=7.1 Hz).

$^{13}C$ NMR (Agilent 150 MHz, MeOD,) δ 176.01, 146.73, 145.88, 138.67, 135.09, 131.24, 119.26, 117.31, 105.34, 104.42, 102.63, 99.57, 80.81, 79.75, 76.48, 76.16, 74.91, 74.57, 73.04, 72.80, 72.59, 71.22, 71.09, 70.45, 70.04, 66.45, 65.54, 62.71, 61.67, 61.47, 54.72, 40.22, 37.33, 35.06, 34.95, 33.42, 33.05, 30.75, 30.62, 30.53, 30.44, 30.38, 29.31, 28.07, 27.09, 25.98, 23.71, 23.03, 14.42.

HRMS $[M+H]^+$ m/z calcd for $C_{53}H_{90}N_5O_{21}^+$ 1132.6123, found 1132.6016.

Thus, Example 14 demonstrates preparation of a GSL modified with a fluorescent tag according to the disclosure using methods of the disclosure.

What is claimed:

1. A method of synthesizing a glycolipid of Formula (I)

(I)

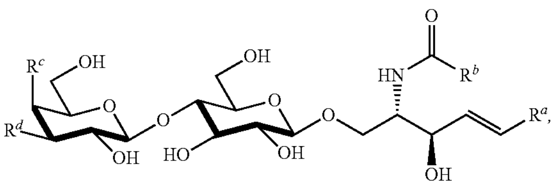

wherein $R^a$ is a $C_{1-30}$alkylene-A;

$R^b$ is $C_{1-30}$alkylene-A';

A and A' are independently H, a fluorescent or molecular tag, or $N_3$;

each of $R^C$ and $R^d$ independently comprise OH or a monosaccharide, disaccharide, trisaccharide, or tetrasaccharide;

the method comprising (a) admixing a glycan intermediate of Formula (II) with an alkene CH═CH—$R^a$ in the presence of Grubbs II catalyst to form an alkene intermediate of Formula (III):

(II)

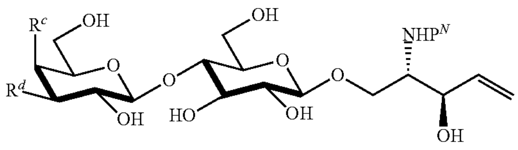

and (III)

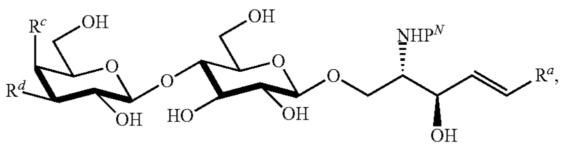

wherein $P^N$ is Boc, Fmoc, Cbz, or Troc, $HP^N$ together form Phth, or $NHP^N$ together form $N_3$;

(b) deprotecting the alkene intermediate of Formula (III) to form a deprotected amine, and (c) reacting the deprotected amine with Cl—C(O)$R^b$, $R^b$C(O)—O—C(O)$R^b$, or HO—C(O) $R^b$ to form the glycolipid of Formula (I).

2. The method of claim 1, wherein at least one of $R^C$ and $R^d$ comprises a monosaccharide, disaccharide, trisaccharide, or tetrasaccharide, and the method comprises reacting a compound (1) with a monosaccharide intermediate under enzymatic elongation conditions to provide the glycan intermediate of Formula (II)

(1)

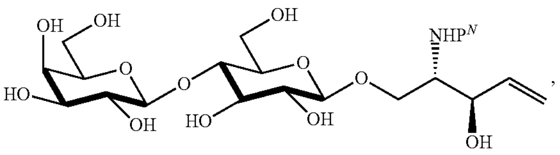

wherein $P^N$ is Boc, Fmoc, or Cbz, $HP^N$ together form Phth, or $NHP^N$ together form $N_3$.

3. The method of claim 2, wherein the enzymatic elongation conditions comprise the presence a glycosyltransferase.

4. The method of claim 3, wherein the glycosyltransferase is selected from the group consisting of PmST1, GlcT, GlcNAcT GalNAcT, or GalT.

5. The method of claim 2, wherein the monosaccharide intermediate is prepared by a method comprising reacting a monosaccharide-1-phosphate with CTP, UTP, or GTP in the presence of a sugar-nucleotide synthase.

6. The method of claim 2, wherein when at least one of $R^C$ and $R^d$ comprises a disaccharide, trisaccharide, or tetrasaccharide, the method further comprises repeating the enzymatic elongation reaction to form the disaccharide, trisaccharide, or tetrasaccharide of the at least one of $R^C$ and $R^d$.

7. The method of claim 2, wherein the compound (1) is prepared by a method comprising admixing a compound (2A) with methanol and sodium methoxide in solution (2A)

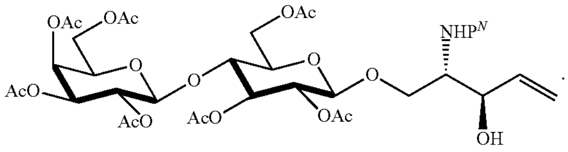

8. The method of claim 7, further comprising coupling a compound (3) to a protected disaccharide of compound (4) to form the compound (2A)

(3)

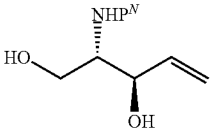

(2)

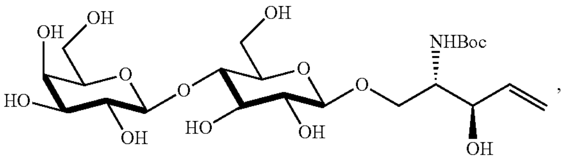

wherein $P^N$ is Boc, Fmoc, or Cbz, $HP^N$ together form Phth, or $NHP^N$ together form $N_3$, and (4)

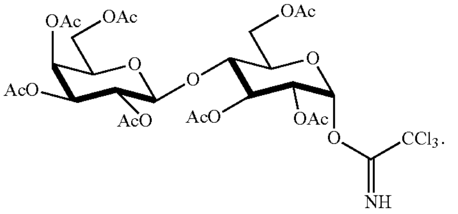

9. The method of claim 1, wherein the alkene CH═CH—$R^a$ is present in an amount of about 5 to about 15 molar equivalents relative to the glycan intermediate of Formula (II).

10. The method of claim 1, wherein the deprotecting in step (b) comprises admixing the alkene intermediate of Formula (III) with $ZnBr_2$, optionally in the presence of a solvent, at room temperature.

11. The method of claim 2, wherein the monosaccharide, disaccharide, trisaccharide, or tetrasaccharide of at least one of $R^C$ and $R^d$ is selected from the group consisting of sialic acid, galactose, and galactosamine.

12. A glycan intermediate of Formula (II)

(II)

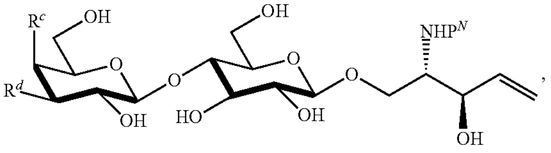

wherein each of $R^C$ and $R^d$ independently comprise OH or a monosaccharide, disaccharide, trisaccharide, or tetrasaccharide; and $P^N$ is Boc, Fmoc, Troc, or Cbz, $HP^N$ together form Phth, or $NHP^N$ together form $N_3$;

with the proviso that when $R^d$ is a monosaccharide or OH and $NHP^N$ together form $N_3$, then $R^C$ is not OH.

13. The glycan intermediate of claim 12, wherein the monosaccharide, disaccharide, trisaccharide, or tetrasaccharide comprises an unnatural sugar.

14. The glycan intermediate of claim 12, wherein the monosaccharide, disaccharide, trisaccharide, or tetrasaccharide comprises sialic acid, galactose, or galactosamine.

15. The glycan intermediate of claim 12 having a structure selected from the group consisting of:

(2.1)

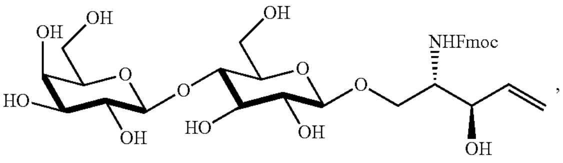

-continued
(2.2)
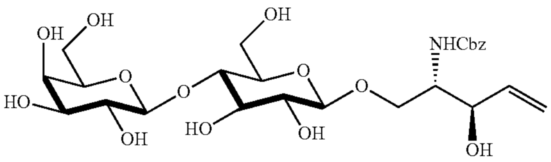
,
(2.3)
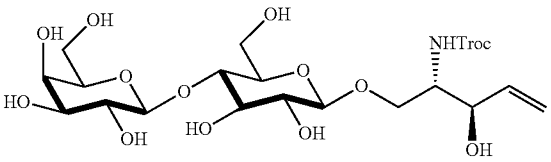
,
(5)
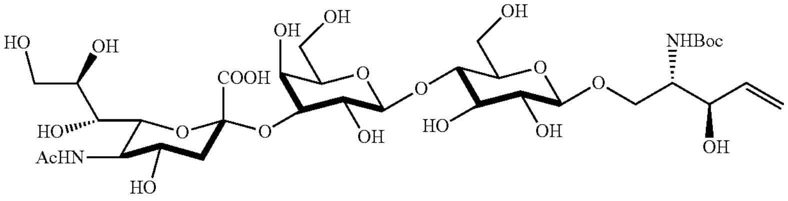
,
(5.1)
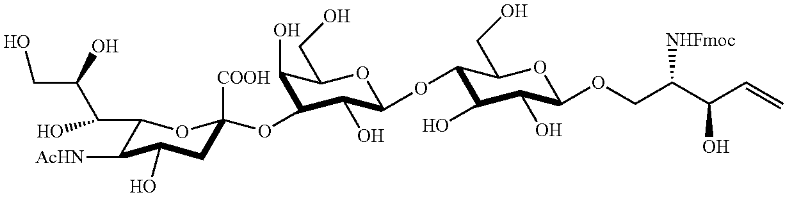
,
(5.2)
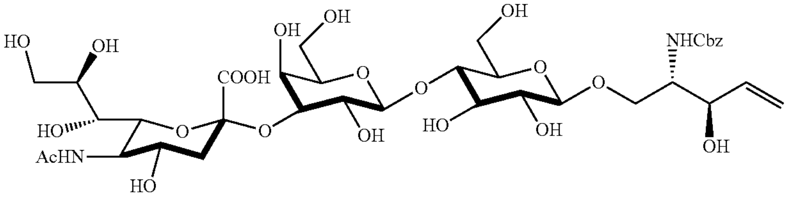
,
(5.3)
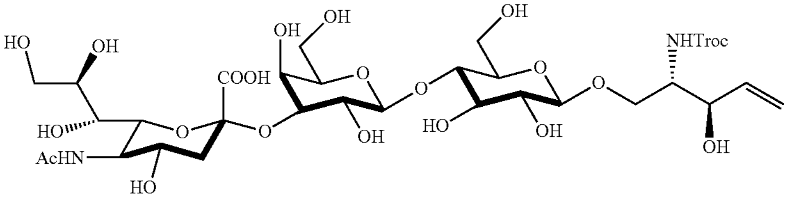
,
(6)
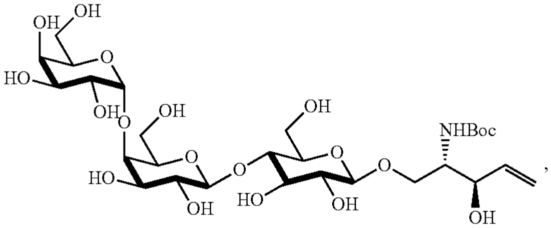
,
(6.1)
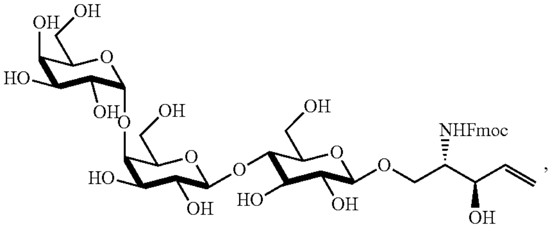
,
(6.2)
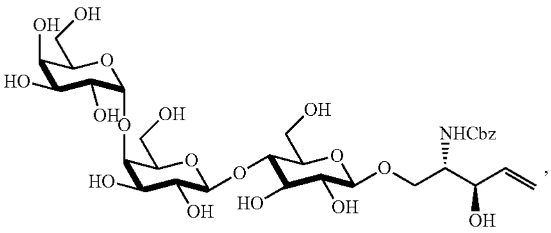
,
(6.3)
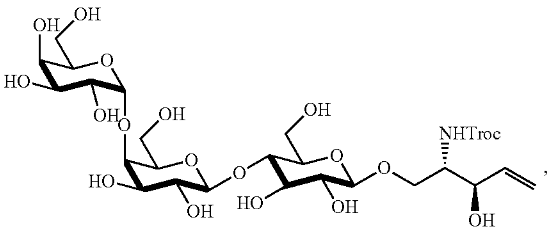
, -continued (7)

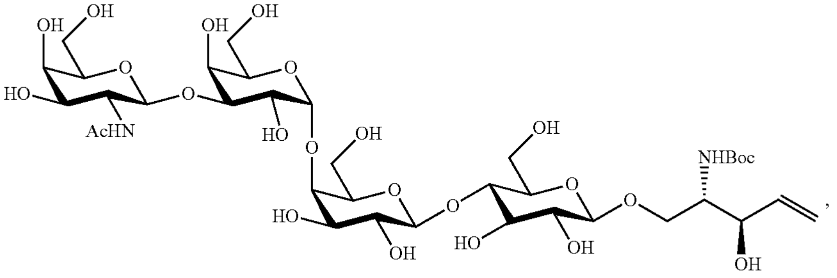

(7.1)

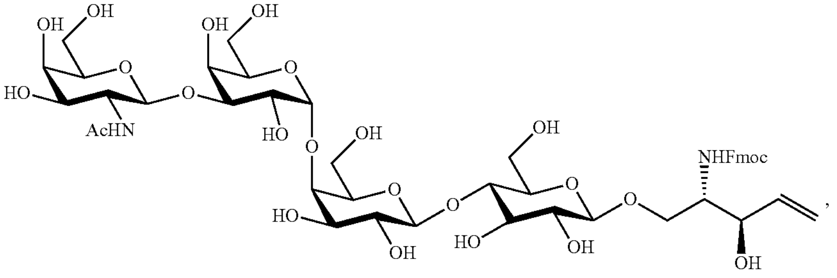

(7.2)

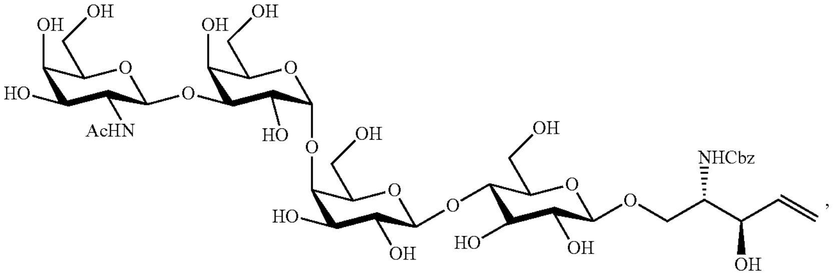

and (7.3)

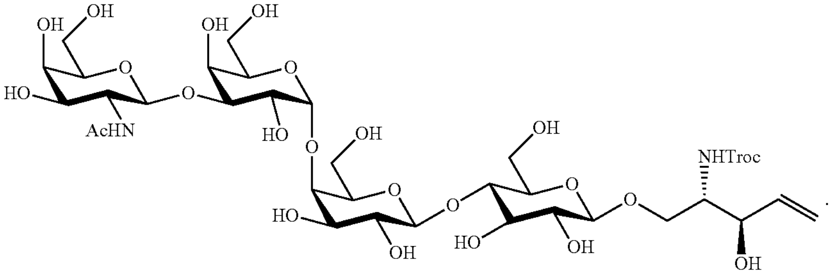

16. An alkene intermediate of Formula (IV)

(IV)

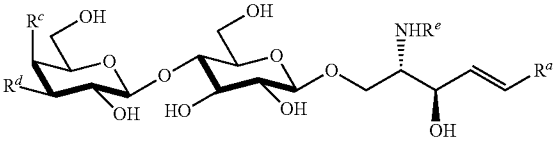

wherein $R^a$ is a $C_{10-20}$alkyl;

each of $R^C$ and $R^d$ independently comprise OH or a monosaccharide, disaccharide, trisaccharide, or tetrasaccharide; and $R^e$ is H, Boc, Fmoc, Troc, or Cbz, $HR^e$ together form Phth, or $NHR^e$ together form $N_3$;

with the provisos that when $R^a$ is $C_{13}$alkyl, $R^C$ is OH, and $R^d$ is a monosaccharide, then $R^e$ is not H, and when $R^a$ is $C_{13}$alkyl and $R^c$ and $R^d$ are both OH, then $NHR^e$ together are not $N_3$ or $NH_2$.

17. The alkene intermediate of claim 16, wherein the monosaccharide, disaccharide, trisaccharide, or tetrasaccharide comprises an unnatural sugar.

18. The alkene intermediate of claim 16, wherein the monosaccharide, disaccharide, trisaccharide, or tetrasaccharide comprises sialic acid, galactose or galactosamine.

19. The alkene intermediate of claim 16, wherein $R^a$ is $C_{13}$alkyl or $C_{11}$alkyl.

20. The alkene intermediate of claim 16 having a structure selected from the group consisting of:

(8)
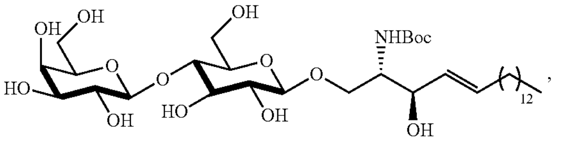
(8.1)
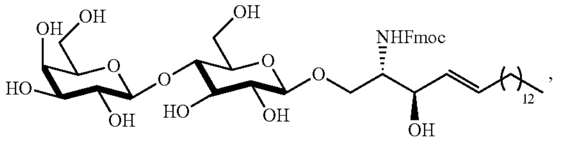
(8.2)
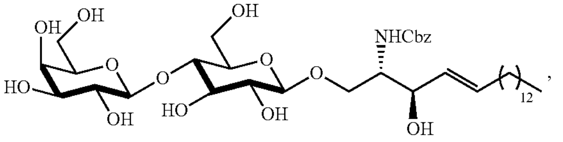
(8.3)
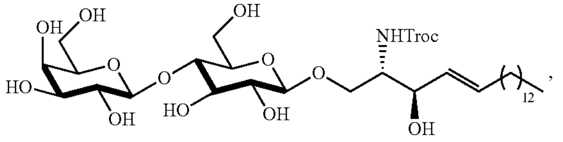
(10)
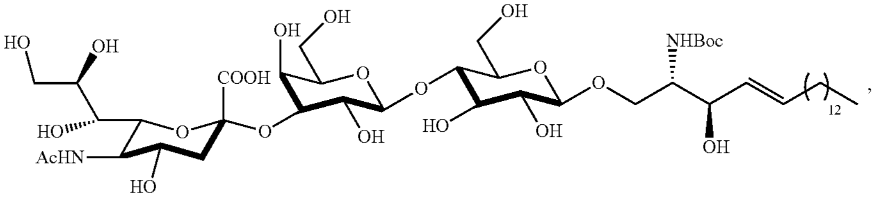
(10.1)
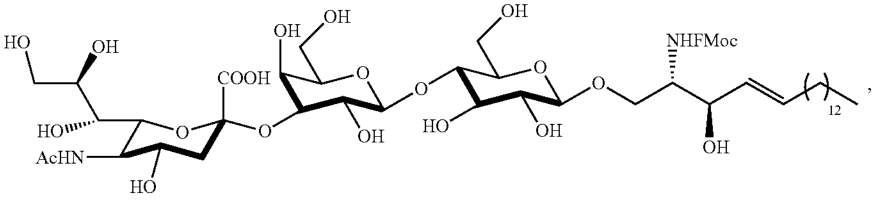
(10.2)
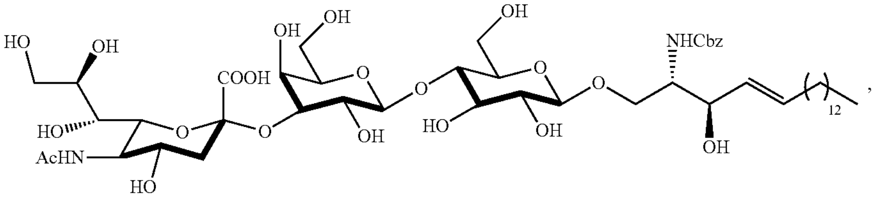
(10.3)
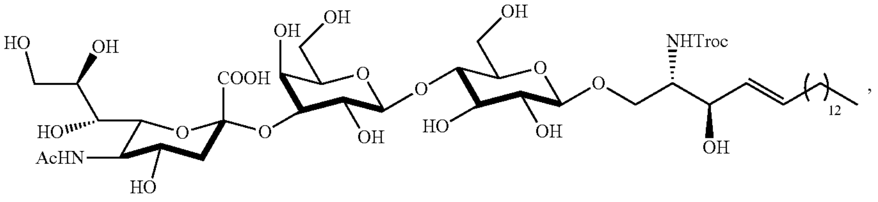
(11)
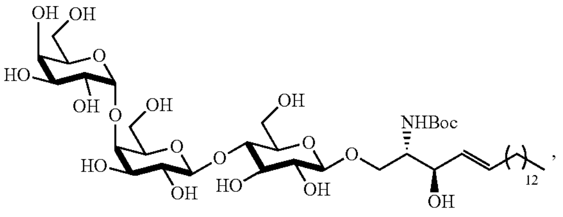
(11.1)
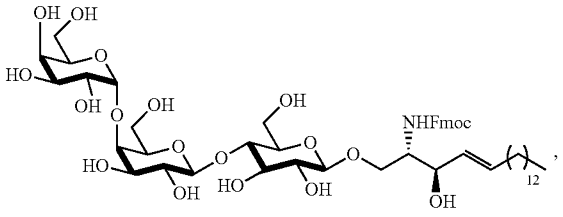

-continued
(11.2)
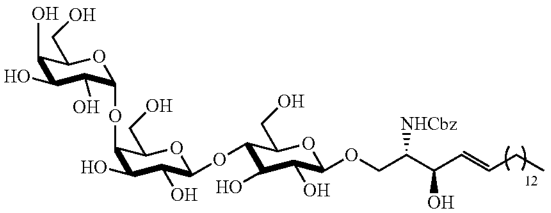
,
(11.3)
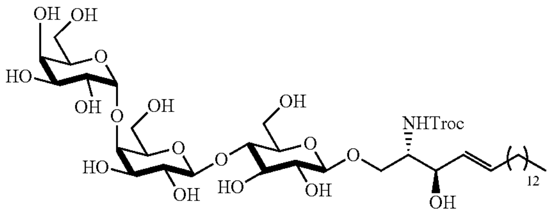
,
(13)
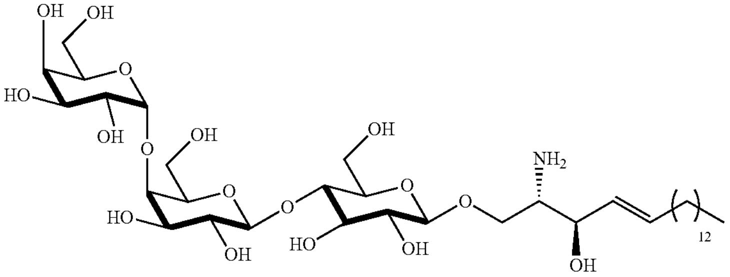
,
(14)
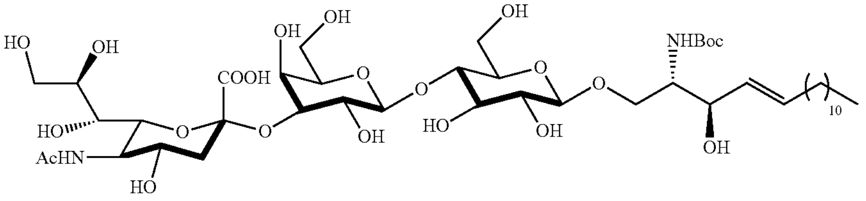
,
(14.1)
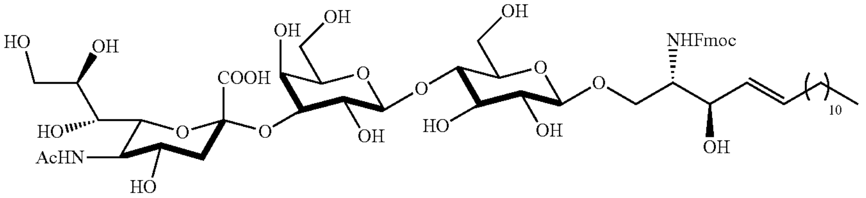
,
(14.2)
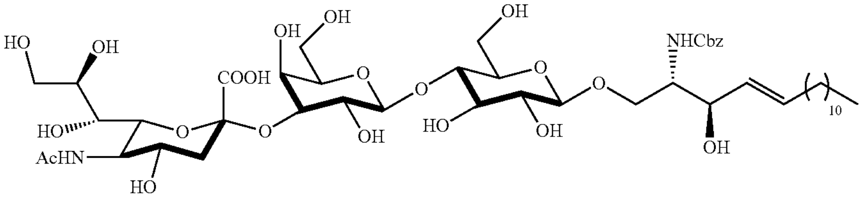
,
(14.3)
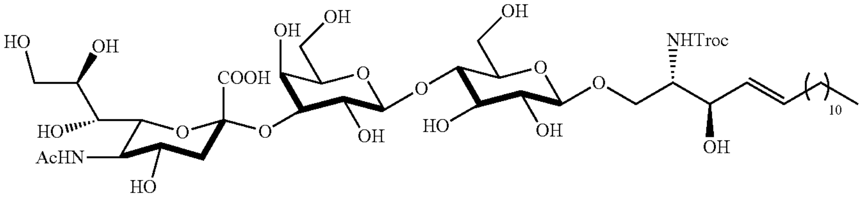
,
(15)
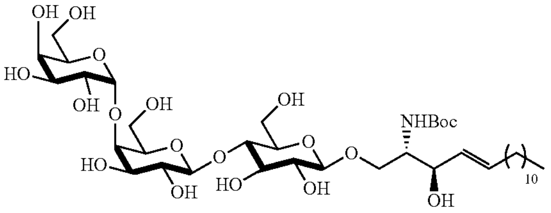
,
(15.1)
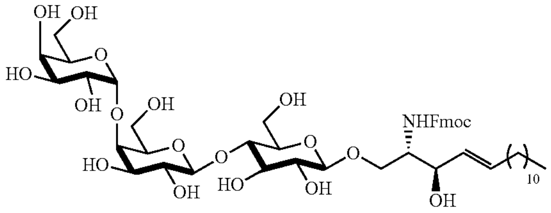
, -continued
(15.2)
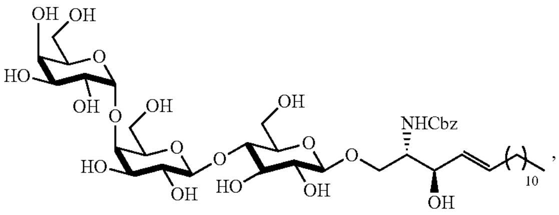
,
(15.3)
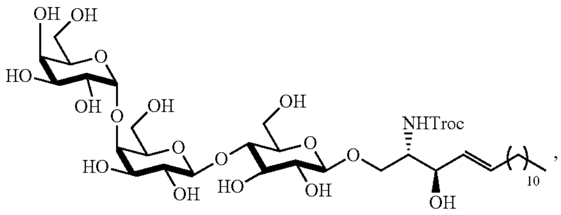
,
(16)
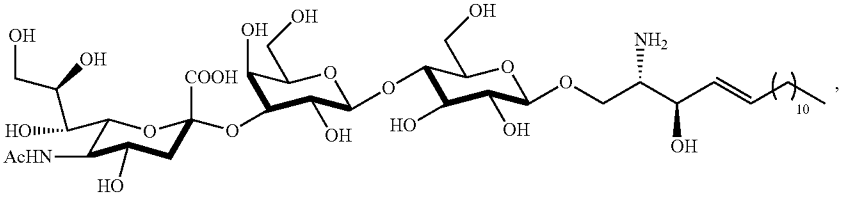
, and
(17)
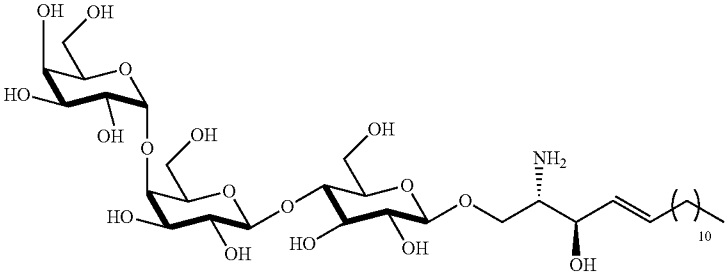
.
* * * * *